(12) United States Patent
Vahabzadeh-Hagh

(10) Patent No.: US 12,390,608 B2
(45) Date of Patent: Aug. 19, 2025

(54) TRACHEOSTOMY SUPPORT SYSTEM

(71) Applicant: The Regents of the University of California, Oakland, CA (US)

(72) Inventor: Andrew Vahabzadeh-Hagh, La Jolla, CA (US)

(73) Assignees: The Regents of the University of California, Oakland, CA (US); The United States of America as represented by the Department of Veterans Affairs, Office of the General Counsel (024), Washington, DC (US)

( * ) Notice: Subject to any disclaimer, the term of this patent is extended or adjusted under 35 U.S.C. 154(b) by 1088 days.

(21) Appl. No.: 17/419,263

(22) PCT Filed: Dec. 30, 2019

(86) PCT No.: PCT/US2019/068970
§ 371 (c)(1),
(2) Date: Jun. 28, 2021

(87) PCT Pub. No.: WO2020/140121
PCT Pub. Date: Jul. 2, 2020

(65) Prior Publication Data
US 2022/0072252 A1 Mar. 10, 2022

Related U.S. Application Data

(60) Provisional application No. 62/786,210, filed on Dec. 28, 2018.

(51) Int. Cl.
*A61M 16/00* (2006.01)
*A61M 16/04* (2006.01)
*A61M 16/08* (2006.01)

(52) U.S. Cl.
CPC ...... *A61M 16/047* (2013.01); *A61M 16/0875* (2013.01); *A61M 2205/3303* (2013.01);
(Continued)

(58) Field of Classification Search
CPC ............ A61M 16/047; A61M 16/0497; A61M 16/0488; A61M 16/0465; A61M 16/0875;
(Continued)

(56) References Cited

U.S. PATENT DOCUMENTS 3,861,158 A * 1/1975 Swain ..................... E02D 27/46
405/172
4,969,470 A * 11/1990 Mohl ..................... A61B 5/021
604/920
(Continued)

FOREIGN PATENT DOCUMENTS

CN 108273168 A 7/2018
DE 102006056946 A1 6/2008

OTHER PUBLICATIONS

ISA/US, "International Search Report and Written Opinion", for Application No. PCT/US19/68970. Mail Date: Jun. 17, 2020; 13 pages.

*Primary Examiner* — Steven M Marsh
(74) *Attorney, Agent, or Firm* — Perkins Coie LLP

(57) ABSTRACT

Disclosed are materials, articles, devices, and methods for manufacture thereof that pertain to a tracheostomy support system. The tracheostomy support system can eliminate torque on the tracheostomy tube and offload pressure caused by the tracheostomy tube on the neck skin of a patient. Additionally, the tracheostomy support system can indicate when pressure or moisture on the skin is at an unsafe level that may predispose the patient to neck skin ulceration, breakdown, or infection. The tracheostomy support system can be automatically adjusted through a closed-loop feedback system or can be manually adjusted.

19 Claims, 16 Drawing Sheets

(52) U.S. Cl.
CPC ........... *A61M 2205/3317* (2013.01); *A61M 2205/3324* (2013.01); *A61M 2205/3331* (2013.01); *A61M 2205/3368* (2013.01); *A61M 2205/581* (2013.01); *A61M 2205/583* (2013.01)

(58) Field of Classification Search
CPC .. A61M 2205/3303; A61M 2205/3317; A61M 2205/3324; A61M 2205/3331; A61M 2205/3368; A61M 2205/581; A61M 2205/583
USPC ............... 604/304, 308; 128/207.17, 207.14; 248/346.2, 49, 51, 52, 58, 65, 68.1, 70, 248/73, 74.1, 74.2
See application file for complete search history.

(56) References Cited

U.S. PATENT DOCUMENTS

| | | | | |
|---|---|---|---|---|
| 4,995,124 | A * | 2/1991 | Wridge, Jr. | A47C 27/18 5/709 |
| 5,163,914 | A * | 11/1992 | Abel | A61M 25/02 128/200.24 |
| 6,647,570 | B1 * | 11/2003 | Ong | A47G 9/1045 5/502 |
| 7,414,536 | B2 * | 8/2008 | Call | A61G 7/05769 340/626 |
| 8,281,788 | B2 * | 10/2012 | Thompson | A61H 31/007 601/149 |
| 8,545,464 | B2 * | 10/2013 | Weston | A61F 13/00059 604/315 |
| 8,974,427 | B2 | 3/2015 | Ballenger | |
| 9,937,310 | B2 * | 4/2018 | Murphy | A61M 16/0875 |
| 10,383,986 | B2 * | 8/2019 | Robinson | A61M 1/74 |
| 11,020,175 | B2 * | 6/2021 | Sharma | A61M 25/10 |
| 11,135,383 | B2 * | 10/2021 | Varga | A61M 16/0051 |
| 2007/0108753 | A1 | 5/2007 | Pang et al. | |
| 2009/0000037 | A1 | 1/2009 | Graebe | |
| 2009/0221914 | A1 * | 9/2009 | Barrett | A61M 5/14216 600/431 |
| 2013/0281773 | A1 * | 10/2013 | Augarten | A61F 5/0013 600/37 |
| 2013/0296769 | A1 * | 11/2013 | Howell | A61F 13/00 604/24 |
| 2018/0250193 | A1 * | 9/2018 | Freeman | A61H 31/005 |
| 2020/0297909 | A1 * | 9/2020 | Suljevic | A61M 1/1565 |
| 2020/0353190 | A1 * | 11/2020 | Browne | A61M 16/0051 |
| 2020/0360690 | A1 * | 11/2020 | Evans | G16H 20/40 |
| 2021/0338944 | A1 * | 11/2021 | Breatnach | A61B 5/15003 |

* cited by examiner

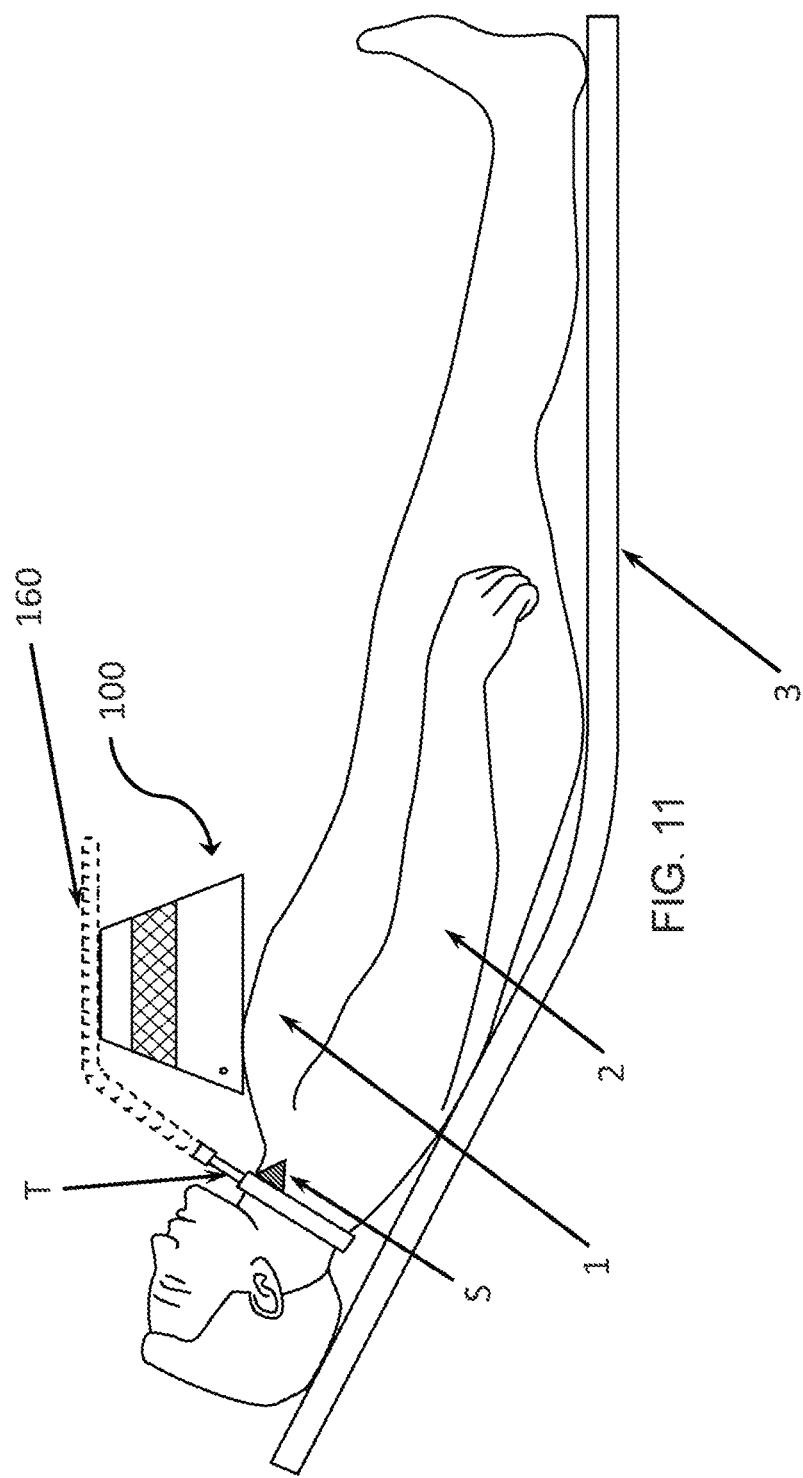

TRACHEOSTOMY SUPPORT SYSTEM

CROSS-REFERENCE TO RELATED APPLICATION

This patent document is a 371 National Phase Application of International Application No. PCT/US2019/068970, filed on Dec. 30, 2019, which claims priority to and benefits of U.S. Provisional Patent Application No. 62/786,210 entitled "TRACHEOSTOMY SUPPORT SYSTEM" filed on Dec. 28, 2018. The entire contents of the aforementioned patent applications are incorporated by reference as part of the disclosure of this patent document.

TECHNICAL FIELD

This patent document relates to systems, devices, and methods for tracheostomy support.

BACKGROUND

A tracheostomy is a surgical procedure to create an opening into the trachea through the neck. A tracheostomy provides an air passage at the opening to aid in breathing when the usual route for breathing is impaired or obstructed. A tube is placed through this opening to provide an airway and to remove secretions from the lungs. The tube, or the tracheostomy tube, may be connected to a ventilator circuit tubing or ventilator machine components to aid in breathing and remove secretions in the trachea.

The ventilator circuit tubing or ventilator machine components inevitably create undesirable torques and pressure forces acting on the patient's tracheostomy tube which can lead to pressure ulcers that lead to skin breakdown, bleeding, infection, and can even cause erosion of the esophagus or large blood vessels leading to death. The ventilator circuit tubing or ventilator machine components can also create torques end exert pressure forces on the ventilator circuit and tracheostomy tube connection which may cause ventilator circuit to disconnect from the tracheostomy tube which might have potentially grave consequences.

Existing clinical tools attempt to address these problems by making, for example, the tracheostomy tube softer or by using devices preventing the ventilator tubing from disconnecting from the tracheostomy tube but these tools do not address the problem of compensating torques and pressure forces acting on various connections and elements of the tracheostomy tube and ventilator system, and, more importantly, acting on the neck skin of a patient.

Thus, there is a pressing need to develop devices, systems, and methods that act to reduce, partially or completely, those harmful torques and pressure forces.

SUMMARY

Disclosed are devices, systems, and methods for compensating torques and pressure forces exerted on a neck skin of a patient by a tracheostomy tube or a ventilator circuit of a lung ventilator. Various examples of embodiments and implementations are disclosed.

For Example:

In some embodiments in accordance with the disclosed technology, a tracheostomy support system (TSS or TS system below) comprises a multilayered pad configured to be disposed between a shield of a tracheostomy tube and a neck of a person. The multilayered pad includes:
a first layer of material configured to provide contact with the neck of a person,
a second layer of material configured to provide contact with the shield of a tracheostomy tube, and
at least one expandable compartment disposed between the first layer of material and the second layer of material.

In some embodiments in accordance with the disclosed technology, a TS system comprises a multilayered pad configured to be disposed between a shield of a tracheostomy tube and a neck of a person. The multilayered pad includes:
a layer of material configured to provide contact with the neck of a person, and
at least one expandable compartment disposed on the layer of material and configured to provide contact with the shield of a tracheostomy tube.

In some embodiments in accordance with the disclosed technology, a TS system comprises:
a multilayered pad configured to be disposed between a shield of a tracheostomy tube and a neck of a person, wherein the multilayered pad comprises:
a layer of material configured to provide contact with the neck of a person, and
at least one expandable compartment disposed on the layer of material and configured to provide contact with the shield of a tracheostomy tube,
wherein the at least one expandable compartment is configured to expand when a gas or a liquid is added to the at least one expandable compartment and the at least one expandable compartment is configured to contract when a gas or a liquid is removed from the at least one expandable compartment,
wherein the system further comprises
an interface configured for addition or removal of at least one of:
a gas,
a liquid, or
a gas and a liquid
to or from the at least one expandable compartment,
wherein the system further comprises
at least one pressure sensor configured to be communicatively coupled to a device which controls the amount of the gas or the liquid in the at least one expandable compartment,
wherein the device is configured to receive pressure data from the at least one pressure sensor in a form of digital or analog signals and is further configured, based on the pressure data, cause the device to remove or add the gas or the liquid to or from the at least one expandable compartment.

In some embodiments in accordance with the disclosed technology, a tracheostomy support system includes at least another expandable compartment.

In some implementations of the tracheostomy support system in accordance with the disclosed technology, the at least another expandable compartment is configured to expand or contract independently from the at least one compartment.

The subject matter described in this patent document can be implemented in specific ways that provide one or more of the following features.

BRIEF DESCRIPTION OF THE DRAWINGS

FIG. 11 shows a tracheostomy support system interfaced with a tracheostomy tube and a tube of a ventilator circuit of a lung ventilator and positioned on the chest of a person.

DETAILED DESCRIPTION

The tracheostomy support system can offload torque and pressure caused by a tracheostomy tube on a neck skin of a patient. Additionally, the tracheostomy support system can indicate when pressure or moisture on the skin is at an unsafe level that may predispose the patient to neck skin ulceration, breakdown, or infection.

The tracheostomy support system can be automatically adjusted through a closed-loop feedback system or be manually adjusted. The closed-loop feedback system can achieve the optimal amount of support no matter which tracheostomy tube or a ventilator circuit of a lung ventilator is used, the build of the patient, or the position of the patient. This may be carried out using a pressure sensor that communicates (e.g., wirelessly) with a pump system that can adjust the tracheostomy support system to minimize torque on the tracheostomy tube and minimize the pressure on the neck skin of the patient.

The tracheostomy support system is very inexpensive and highly customizable. The tracheostomy support system solves the problem of pressure and torque on the neck skin of the patient by providing a support for the tracheostomy tube and ventilator circuit tubing. This support reduces torque on the tracheostomy tube and therefore reduces pressure on the neck skin of the patient, thus reducing the chance of ulcers or other neck skin or soft tissue damage. The tracheostomy support system can function in a closed loop with a pressure sensor that communicates with the system to achieve the optimal amount of support. The closed-loop feedback system can adjust for any tracheostomy tube or circuit, body build, or patient positioning. The tracheostomy support system can be used anywhere a tracheostomy tube is connected to a ventilator circuit of a lung ventilator. Embodiments that include a tracheostomy support system for non-ventilator dependent patients are also described.

Figure 1A:
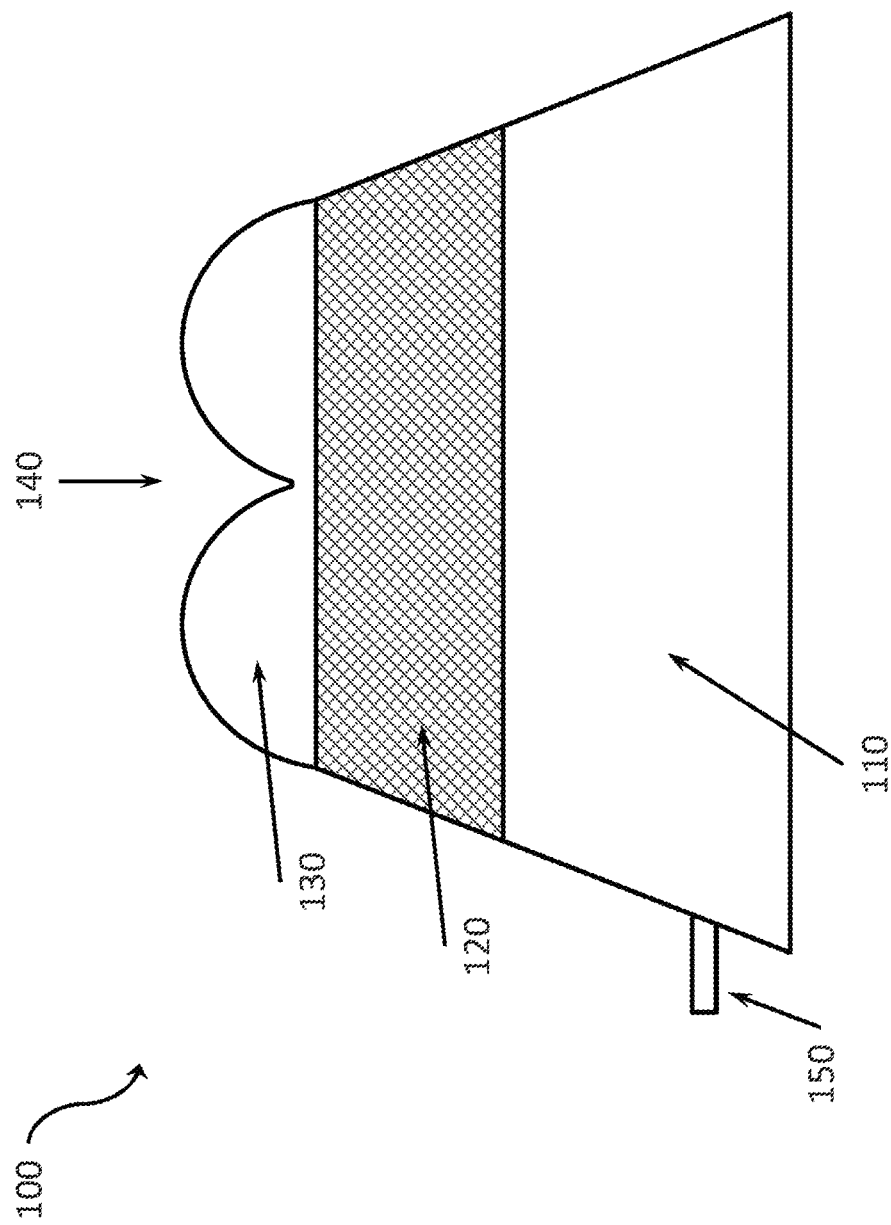
FIG. 1A and FIG. 1B show front views of a tracheostomy support system according to an embodiment.

FIG. 1A shows a front view of an example embodiment of a tracheostomy support system in accordance with the technology described in the present application, labeled system 100.

The system 100 includes:
a base section 110;
a top section 130; and
an expandable compartment 120 disposed between the base section 110 and the top section 130.

In some implementations of the tracheostomy support system 100, the base section 110 is configured to be disposed on one of
a chest of a person, a table, or an articulated stand.

In some implementations of the tracheostomy support system 100, the top section 130 is configured for contact with at least one of
a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

FIG. 1A also shows that, in some implementations of the tracheostomy support system 100, the top section 130 of the system 100 is configured to have a trough 140 adapted for contact with at least one of
a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

FIG. 1A also shows that, in some implementations, the system 100 is configured to have an interface 150 which can be used to inflate or deflate the expandable compartment 120. For example, in some implementations of the system 100, the interface 150 is configured for addition or removal of a gas to or from the expandable compartment 120. For example, in some implementations of the system 100, the interface 150 is configured for addition or removal of a liquid to or from the expandable compartment 120. For example, in some implementations of the system 100, the interface 150 is configured for addition or removal of a gas or a liquid to or from the expandable compartment 120.

Figure 1B:
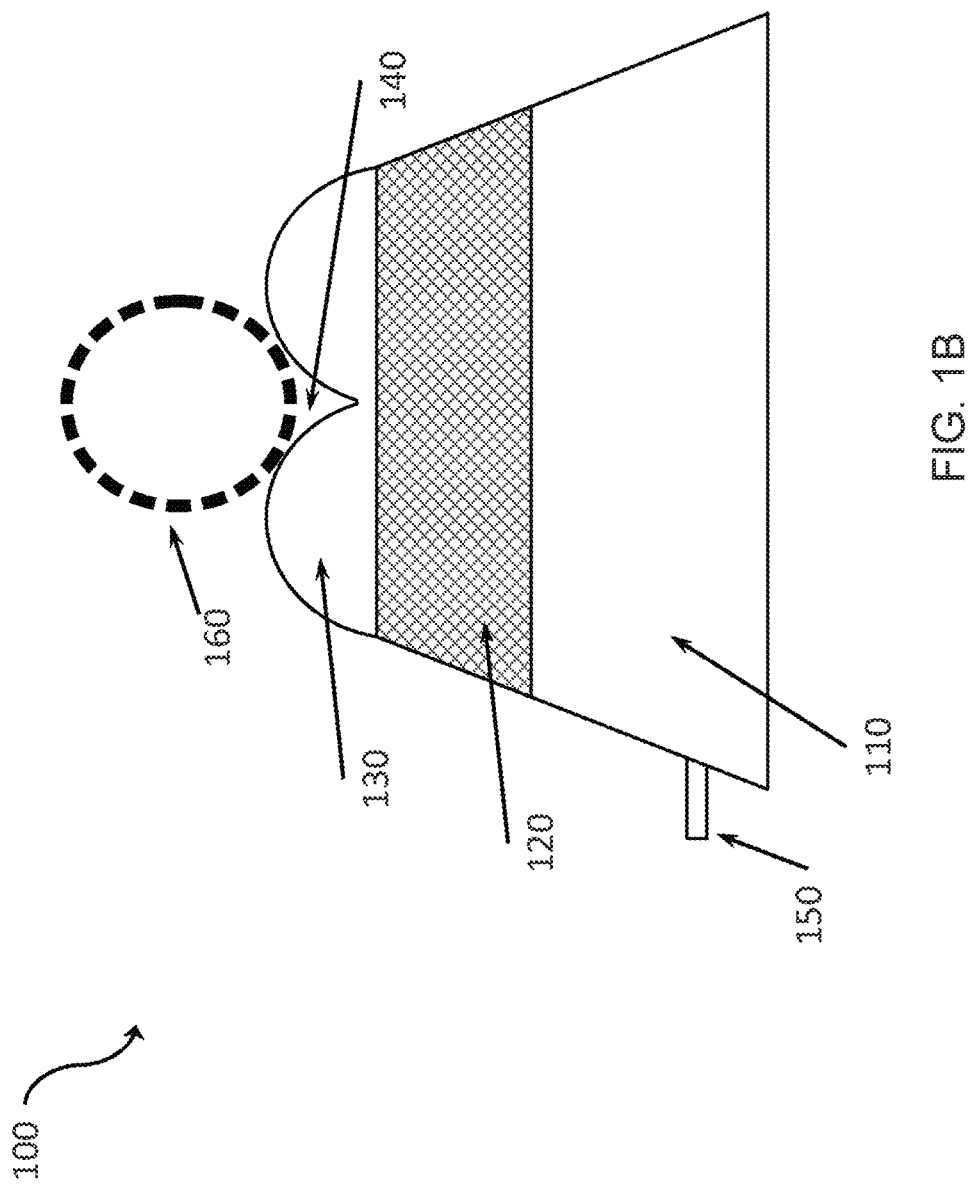

FIG. 1B shows a front view of the tracheostomy support system 100. FIG. 1B shows the top section 130 of the system 100 interfaced with a tube 160 of a ventilator circuit of a lung ventilator. As illustrated in FIG. 1B, the tube 160 is interfaced with the trough element 140 of the top section 130 of the system 100.

Figure 2A:
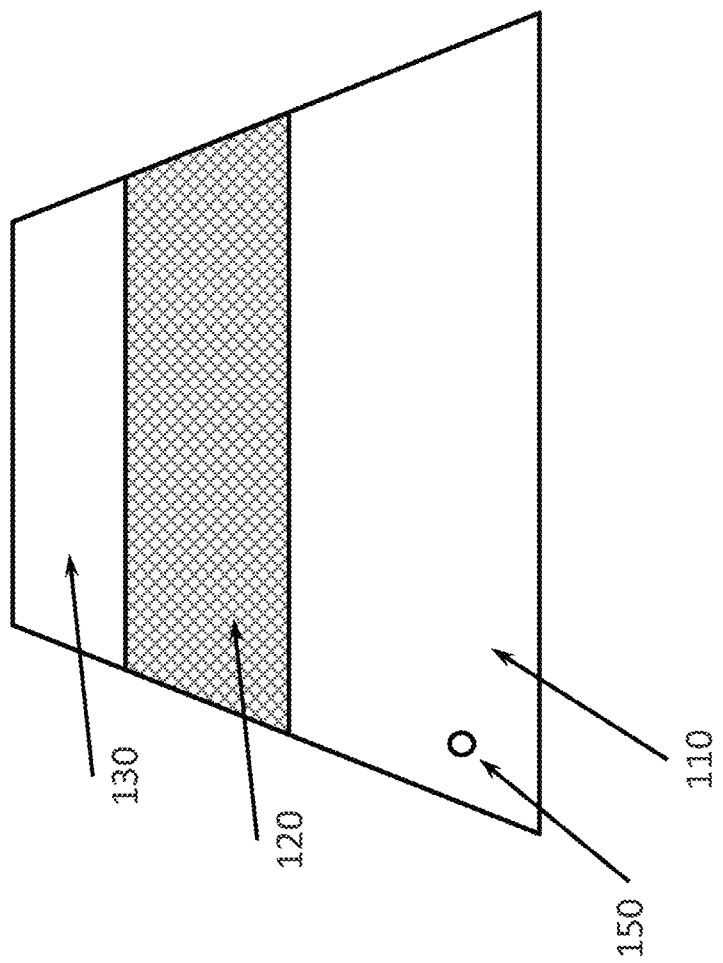
FIG. 2A and FIG. 2B show side views of the tracheostomy support system according to the embodiment shown in FIGS. 1A and 1B.

FIG. 2A shows a side view of the tracheostomy support system 100.

Figure 2B:
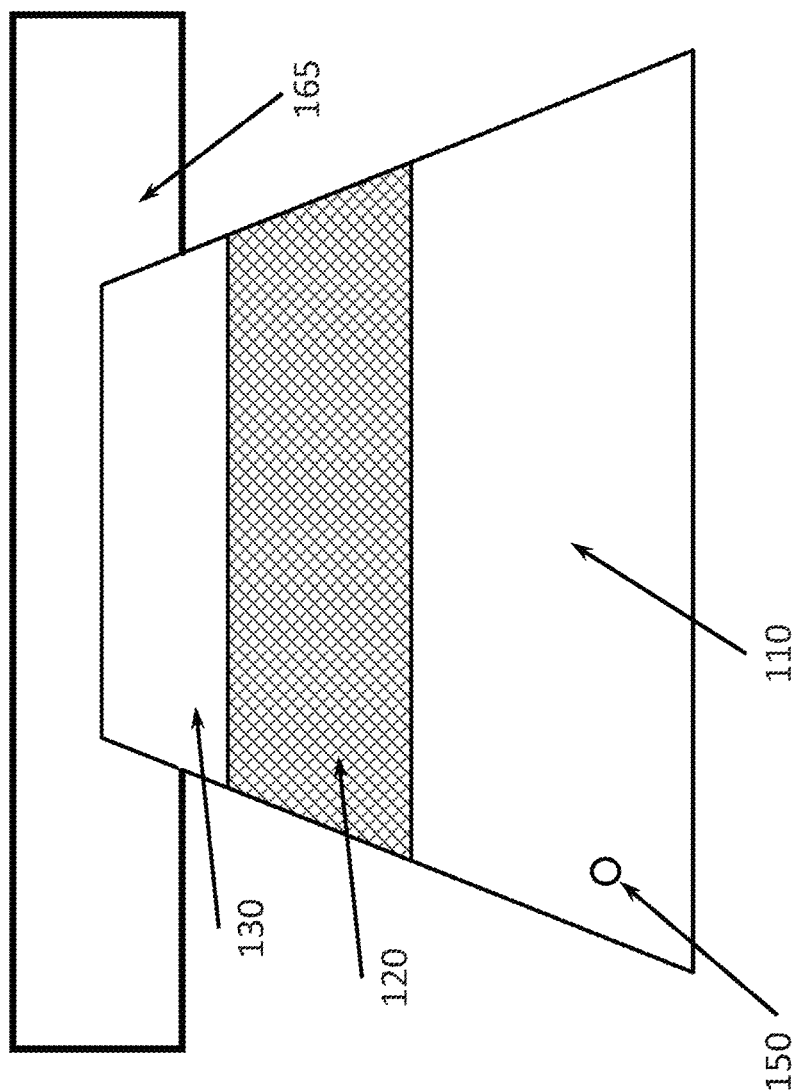

FIG. 2B shows a side view of the tracheostomy support system 100 interfaced with an element 165 of a ventilator circuit of a lung ventilator.

The base section 110 of a tracheostomy support system can be cubical, cylindrical, spherical, pyramidal, trapezoidal, or crescentic in shape. The base section 110 can also have any other shape. The base section 110 can have a sufficiently high degree of bendability and/or deformability to conform to the shape of the chest of a patient, for example, or to another surface under the base section 110. The base section 110 can be of various sizes to adapt to the patient's body, build, height, age, and nutritional status. The base section 110 can distribute the pressure from the tracheostomy tube and ventilator circuit connection on to the patient's chest. The base section 110 can alternatively distribute the pressure on to an articulating stand to varying degrees depending on the clinical needs of the patient. In some embodiments, a trapezoidal shape of the base section 110 is used to increase the surface area upon which force is distributed, reducing the overall pressure to a particular region.

The base section 110 can be interchangeable with other base sections having other shapes and/or sizes. For example, a cubic base section can be swapped out with a trapezoidal base section providing a larger area of contact with the chest of a patient compared to that provided by the cubic base section. Different base sections allow different pressure distributions and configurations to be used. These configurations and pressure distributions are advantageous over a long period of time to increase circulation/perfusion of blood in soft tissues of a patient and increase comfort of the patient.

The base section can be made, for example, using disposable or recyclable materials such as, for example, polypropylene, olefin, silicone, ethylene propylene (EPDM), plastics such as polyvinylchloride (PVC), ethylene vinyl acetate (EVA), styrene ethylene butylene styrene, copolyester ether, nitrile butadiene rubber, polyethylene, polyethylene terephthalate (PET), high-density polyethylene (HDPE), low-density polyethylene (LDPE), polystyrene, polycarbonate, silk, nylon, polytetrafluoroethylene.

The material of the base section can vary depending on its anticipated use (e.g., length of time). For example, polyethylene may be used for short-term applications where single use recyclability is important whereas longer anticipated use may incorporate more durable materials such as silicone.

The base section can incorporate a material with some grip to keep the base section stationary. Materials with higher coefficient of friction such as silicone can be incorporated into the base section as well.

As shown in FIGS. 1A, 1B, 2A, and 2B, the expandable compartment 120 of a tracheostomy support system is placed over the base section 110. In some embodiments, the expandable compartment 120 supports the top section 130 having a trough 140.

In some embodiments, the expandable compartment 120 has a hollow interior. In some embodiments, the expandable compartment 120 has an interior volume at least partially filled with a material, e.g. one of the materials mentioned above.

In some embodiments, the expandable compartment 120 is replaced by an expandable layer of material 120' which can be made, for example, using one or more of the aforementioned materials and/or other materials, that expand by insertion or contract by removal of a gas (e.g., air) or a liquid (e.g., water). The expandable layer of material may be composed, for example, of a composite foam material that has air pockets such as polyurethane foam (PU), reticulated polyurethane, memory foam, and latex foam. Other such materials include, for example, neoprene, PVC, polyethylene foams (PE), cross-linked polyethylene foam (XLPE), Microcell Urethane Foam. The air pockets can expand or can deflate to adjust the height or level of the tracheostomy tube.

In the text below, the term "expandable compartment" can be used in place of the term "expandable layer". In the text below, the term "expandable layer" can be used in place of the term "expandable compartment". In the text below, the term "liquid" can be used in place of the term "gas". In the text below, the term "gas" can be used in place of the term "liquid". In the text below, the term "multilayer pad" can be used in place of the term "multilayered pad" and, vice versa, the term "multilayered pad" can be used in place of the term "multilayer pad".

The removal or addition of a gas causes the contraction or expansion, respectively, of the expandable layer. The contraction and expansion of the expandable layer adjusts the height or thickness of the expandable layer. By controlling the height of the expandable layer, the pressure on the patient from the tracheostomy tube is minimized or eliminated. The expandable layer may contract and expand with gas or liquid insufflation, instillation, or deflation. While the expandable layer of a tracheostomy support system can change its size and/or shape due to its contraction or expansion, the base section and the top section of the tracheostomy support system can, for example, essentially maintain their size and form fixed.

The height of a tracheostomy support system or amount of support it provides can be adjusted by removing or adding a gas (e.g., air) from or to the expandable layer. The addition or removal of the gas from the expandable layer can be done manually or in an automated fashion. For example, the amount and level of support can be controlled using a pressure sensor attached to a tracheostomy tube or the patient's skin. For example, the pressure sensor can be wirelessly coupled to a system which controls the amount of a gas in the expandable layer. The readings from the pressure sensor indicate whether the system should remove or add the gas from/to the expandable layer.

An external motor or an internal motor of a tracheostomy support system can be used to add or remove a gas to or from the expandable layer. The power for the motor comes from a power source. Power source can be batteries, solar power, or any other voltage source (e.g., a wall adapter). The power source can also harness energy from other devices surrounding the patient. In some embodiments, kinetic energy derived from the ventilator circuit or the suction machine can be used to power the motor.

The motor can activate a piston, pump, turbine, knob, syringe, aerosol, or the like to cause addition or removal of a gas to/from the expandable layer. Alternatively, the piston, pump, turbine, knob, syringe, aerosol, or the like can be user-operated to manually adjust the thickness or height of the expandable layer.

The expandable layer can also include an exhaust outflow valve through which the gas inside it can be removed into a reservoir to cause the contraction of the expandable layer. The exchange of the gas between the expandable layer and the reservoir can be done in an environment that is sealed to reduce contaminants. The environment can also define maximum and minimum levels of contraction and expansion for the expandable layer.

The expandable layer can include an interface 150 from which a gas or a liquid can be exchanged. In some embodiments, the gas or the liquid (or both, separately or simultaneously) is taken into the expandable layer through the interface 150. The gas or the liquid in the expandable layer can exit through the interface 150. Additionally, the gas or the liquid in the expandable layer may exit through the exhaust outflow valve. The interface 150 can also be connected to the base section 110 or the top section 130. The interface 150 can be disposed on any of the base section 110, the expandable compartment 120 or the top section 130.

In the system 100, the top section 130 having the trough 140 is placed over the expandable compartment 120. The trough is configured to interface with the tracheostomy and ventilator circuit tubing, as shown in FIG. 1B. The trough also supports and stabilizes the circuit connections. The form of the trough allows the ventilator circuit tubing to rest on top of the expandable layer and base section. The trough can have, for example, a curvilinear or semicircle, wedge, cleft, square, rectangular or trapezoidal notch form. The trough can have any other form. The top section may be made of a soft or absorbent material such as, for example, polyurethane foam (PU), reticulated polyurethane, memory foam, and latex foam, neoprene, PVC, polyethylene foams (PE), cross-linked polyethylene foam (XLPE), Microcell Urethane Foam, and other materials. In some embodiments, the trough forms obtuse or acute angles to provide support for the tracheostomy and ventilator circuit tubing.

Figure 3A:
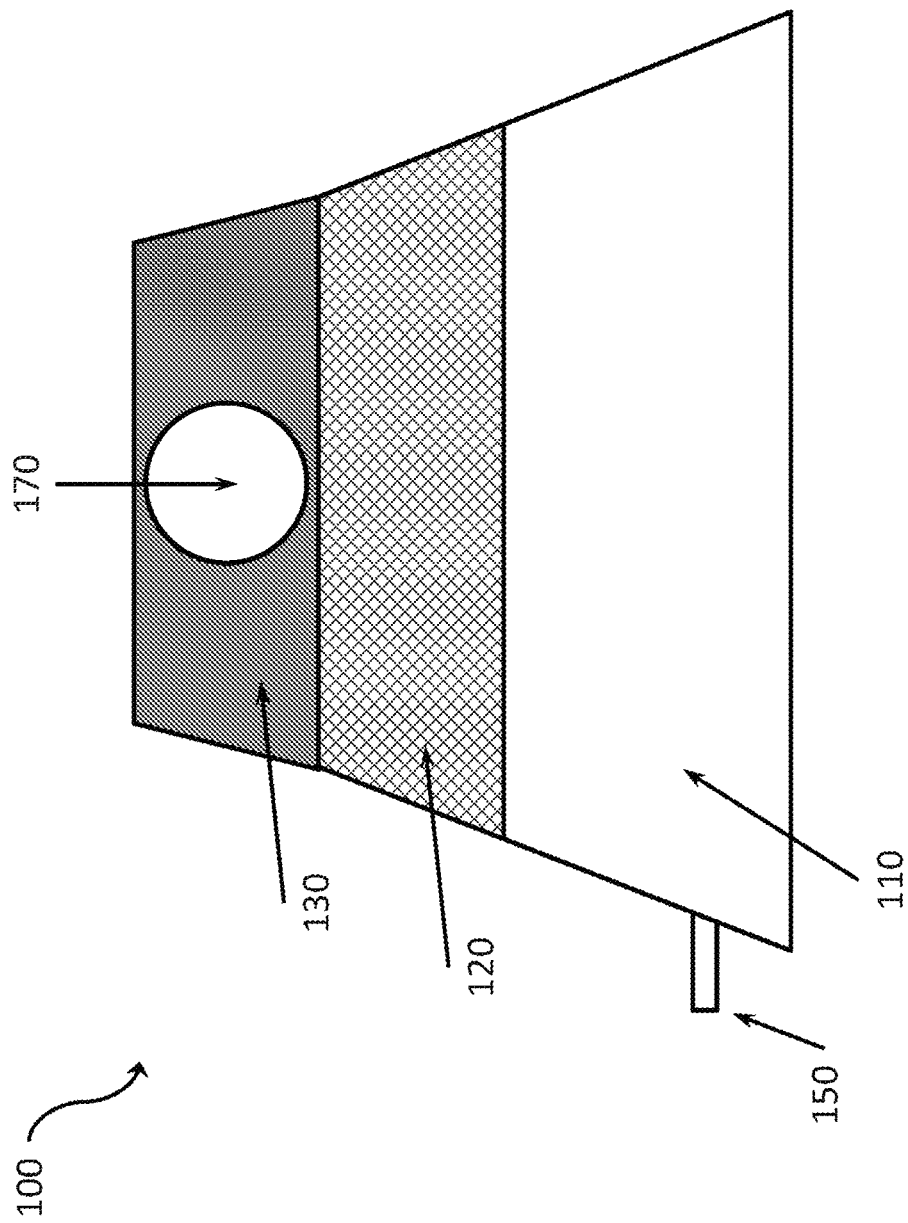
FIG. 3A and FIG. 3B show front views of a tracheostomy support system according to some embodiments.

FIG. 3A shows a front view of an implementation of the tracheostomy support system 100 in which the top section 130 has a hollow channel 170 inside, wherein the hollow channel 170 is adapted for contact with at least one of
  a tube of a ventilator circuit of a lung ventilator, a connection of a ventilator circuit of
  a lung ventilator, an element of a ventilator circuit of a lung ventilator, an element of
  a lung ventilator, a tracheostomy tube, a connection of a tracheostomy tube, or an
  element of a tracheostomy tube.

Figure 3B:
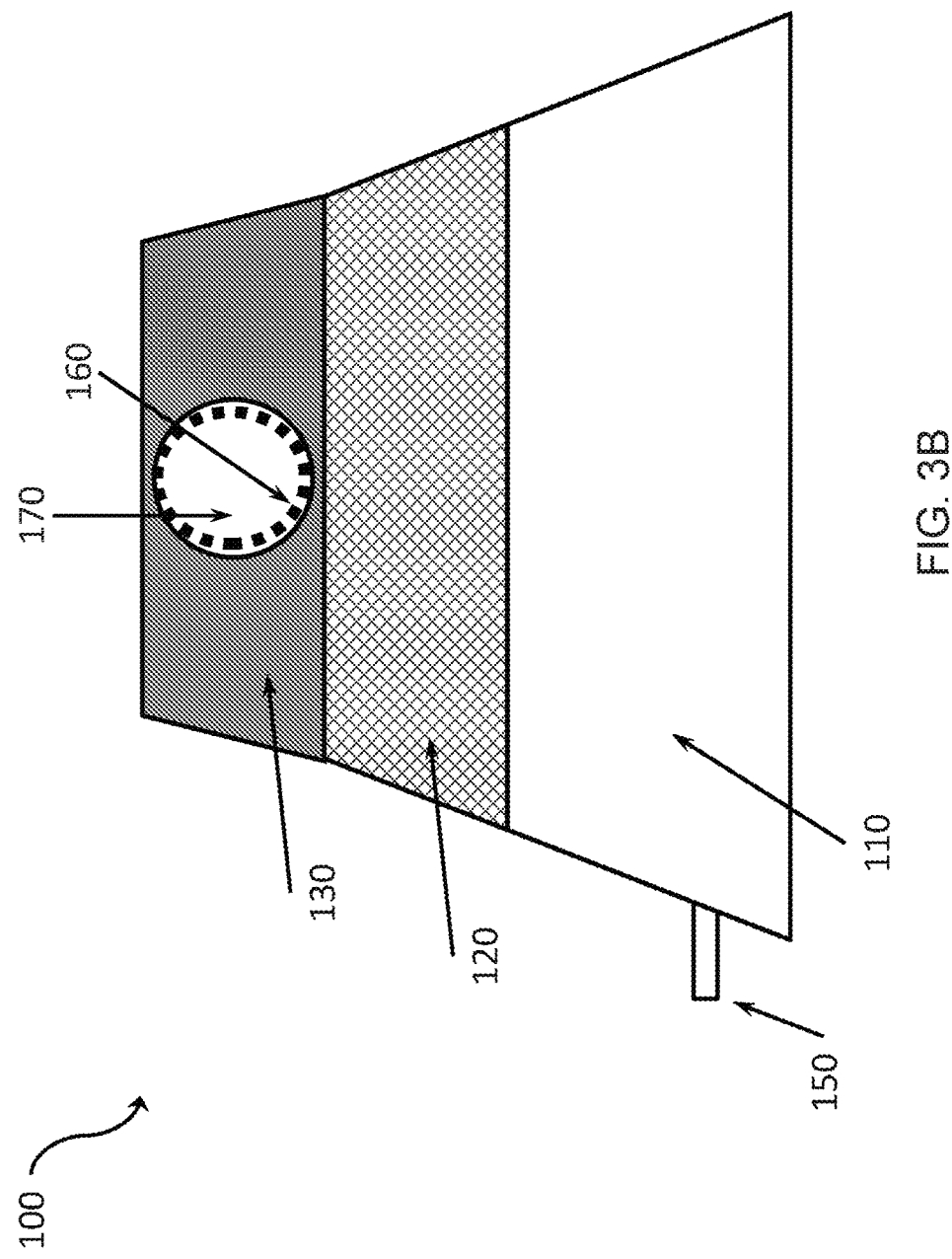

FIG. 3B shows the top section 130 of the system 100 interfaced with a tube 160 of a ventilator circuit of a lung ventilator. As illustrated in FIG. 3B, the tube 160 is interfaced with the hollow channel element 170 of the top section 130 of the system 100.

Figure 4:
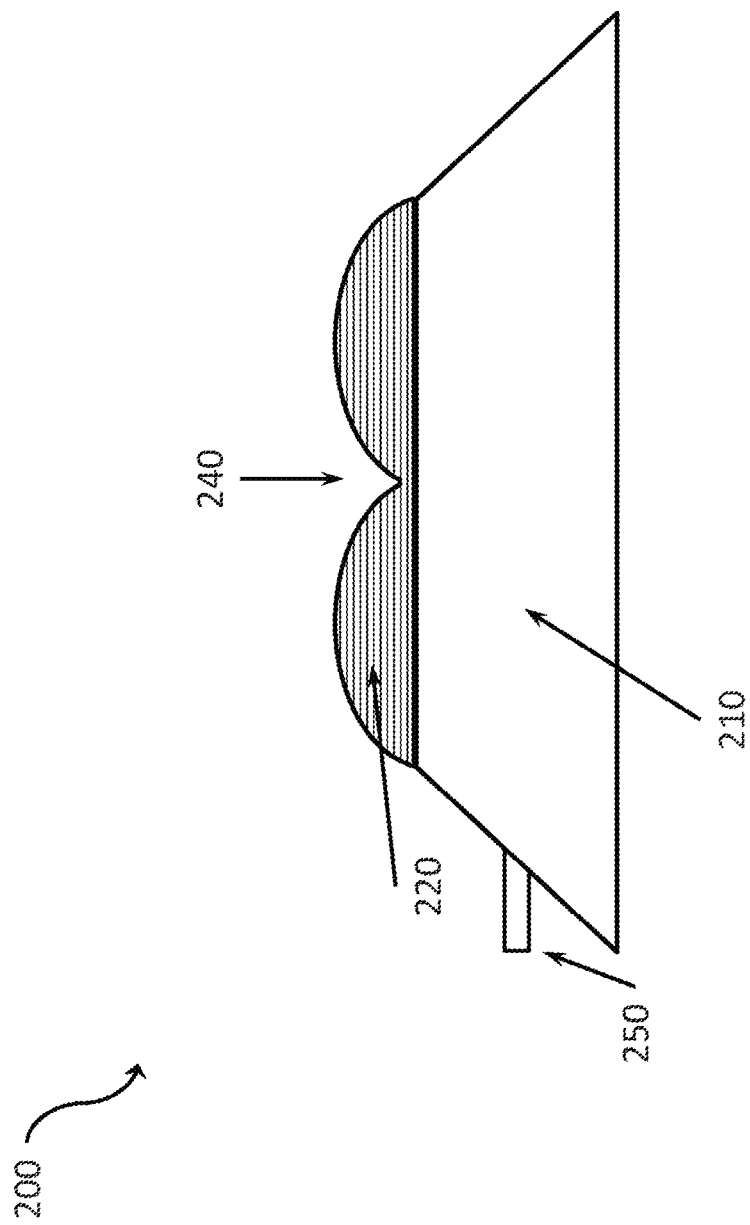
FIG. 4 shows a front view of a tracheostomy support system according to some embodiments.

FIG. 4 shows a view of an example embodiment of a tracheostomy support system in accordance with the technology described in the present application, labeled system 200. The system 200 includes:
  a base section 210; and
  an expandable compartment 220 disposed on the base section 210.

In some implementations of the tracheostomy support system 200, the base section 210 is configured to be disposed on one of
  a chest of a person, a table, or an articulated stand.

In some implementations of the tracheostomy support system 200, the top section 230 is configured to be interfaced with at least one of
  a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

FIG. 4 also shows that, in some implementations of the tracheostomy support system 200, the top section 230 of the system 200 is configured to have a trough 240 adapted for contact with at least one of
  a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

FIG. 4 also shows that, in some implementations, the system 200 is configured to have an interface 250 which can be used to inflate or deflate the expandable compartment 220. For example, in some implementations of the system 200, the interface 250 is configured for addition or removal of a gas to or from the expandable compartment 220. For example, in some implementations of the system 200, the interface 250 is configured for addition or removal of a liquid to or from the expandable compartment 220. For example, in some implementations of the system 200, the interface 250 is configured for addition or removal of a gas or a liquid (or both, separately or simultaneously) to or from the expandable compartment 220.

Figure 5:
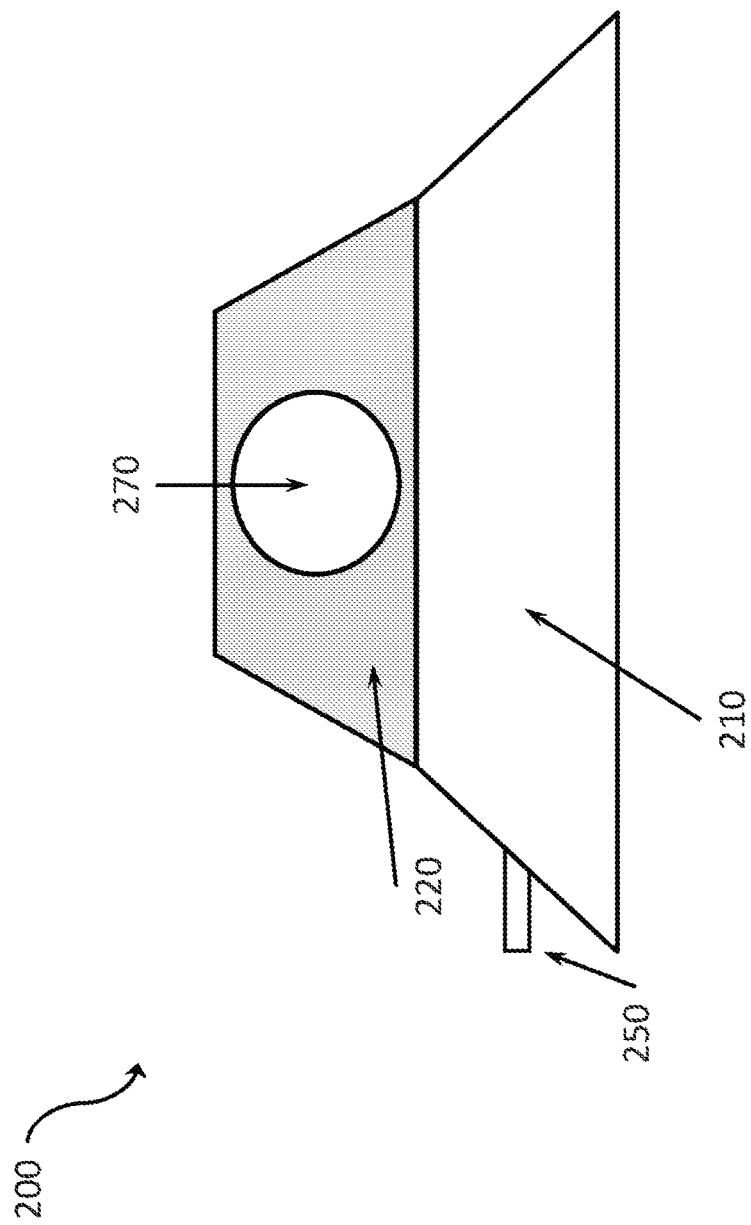
FIG. 5 shows a front view of a tracheostomy support system according to some embodiments.

FIG. 5 shows a front view of an implementation of the tracheostomy support system 200 in which the expandable compartment 220 has a hollow channel 270 inside, wherein the hollow channel 270 is adapted for contact with at least one of
  a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

Figure 6:
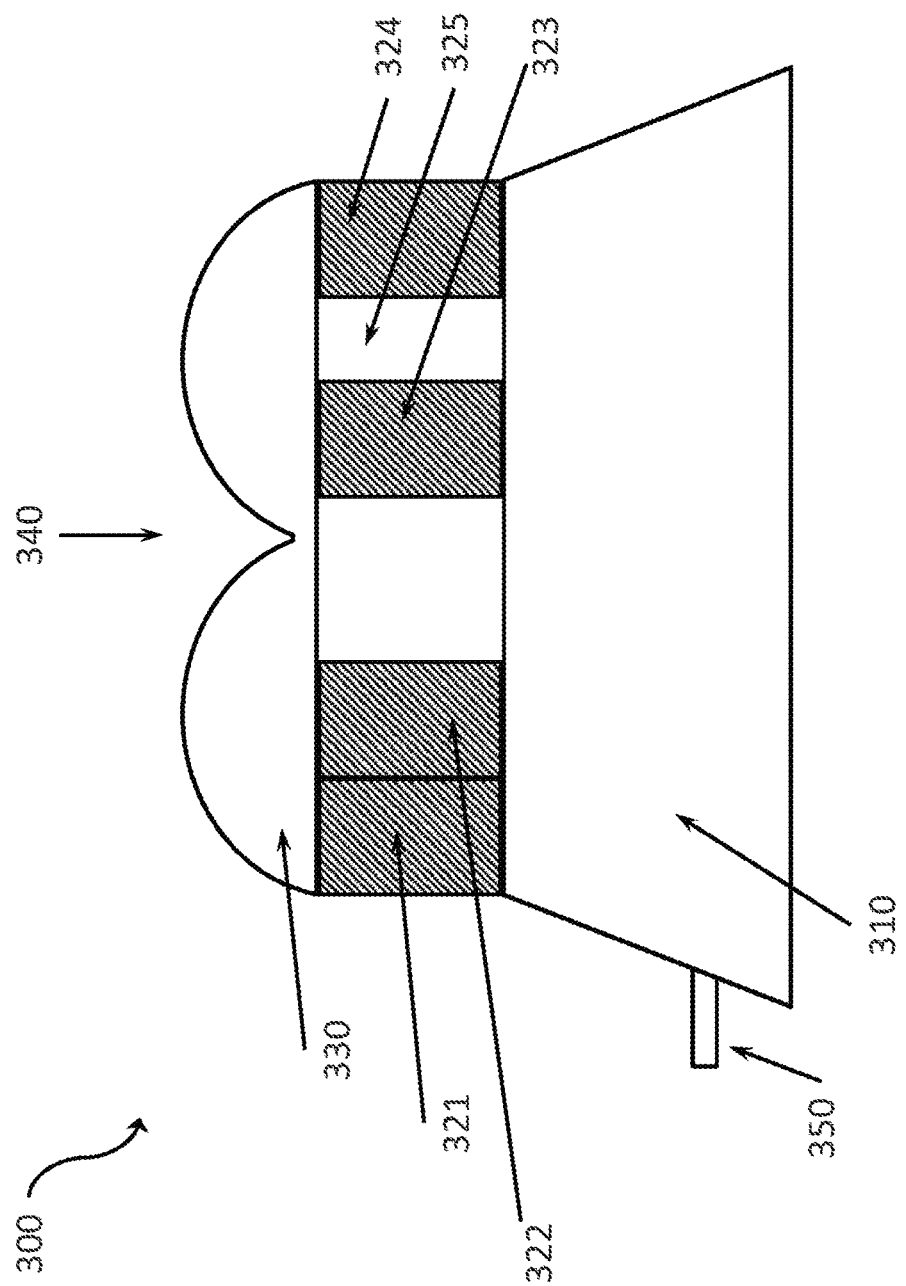
FIG. 6 shows a front view of a tracheostomy support system according to some embodiments.

FIG. 6 shows a front view of an example embodiment of a tracheostomy support system in accordance with the technology disclosed in the present application, labeled system 300. The system 300 includes:
  a base section 310;
  a top section 330;
  an expandable compartment 321 disposed between the base section 310 and the top section 330; and
  at least another expandable compartment 322 disposed between the base section 310 and the top section 330.

FIG. 6 shows that the system 300 also includes expandable compartments 323 and 324 disposed between the base section 310 and the top section 330. The number of the expandable compartments in the system 300 can be larger or can be smaller than the number of compartments shown in FIG. 6. As shown in FIG. 6, some of the expandable compartments (e.g., 321, 322 in FIG. 6) contact each other, while other expandable compartments (e.g., 323, 324 in FIG. 6) are not in contact with each other. As shown in FIG. 6, some of the compartments, whether they contact each other or not, can have a gap between them (e.g., gap 325 in between compartments 323 and 324 in FIG. 6).

FIG. 6 also shows that, in some implementations of the tracheostomy support system 300, the top section 330 of the system 300 is configured to have a trough 340 adapted to interface with at least one of
  a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

FIG. 6 also shows that, in some implementations, the system 300 is configured to have an interface 350 which can be used to inflate or deflate at least one of the expandable compartments. For example, in some implementations of the system 300, the interface 350 is configured for addition or removal of a gas to or from at least one of the expandable compartments. For example, in some implementations of the system 300, the interface 350 is configured for addition or removal of a liquid to or from at least one of the expandable compartments. For example, in some implementations of the system 300, the interface 350 is configured for addition or removal of a gas or a liquid (or both, separately or simultaneously) to or from at least one of the expandable compartments. In some implementations of the system 300, addition or removal of a gas (or a liquid, or both, separately or simultaneously) to or from at least one of the expandable compartments (e.g., compartment 321) is performed independently from addition or removal of a gas (or a liquid, or both, separately or simultaneously) to or from at least another expandable compartment (e.g., compartment 322).

Figure 7A:
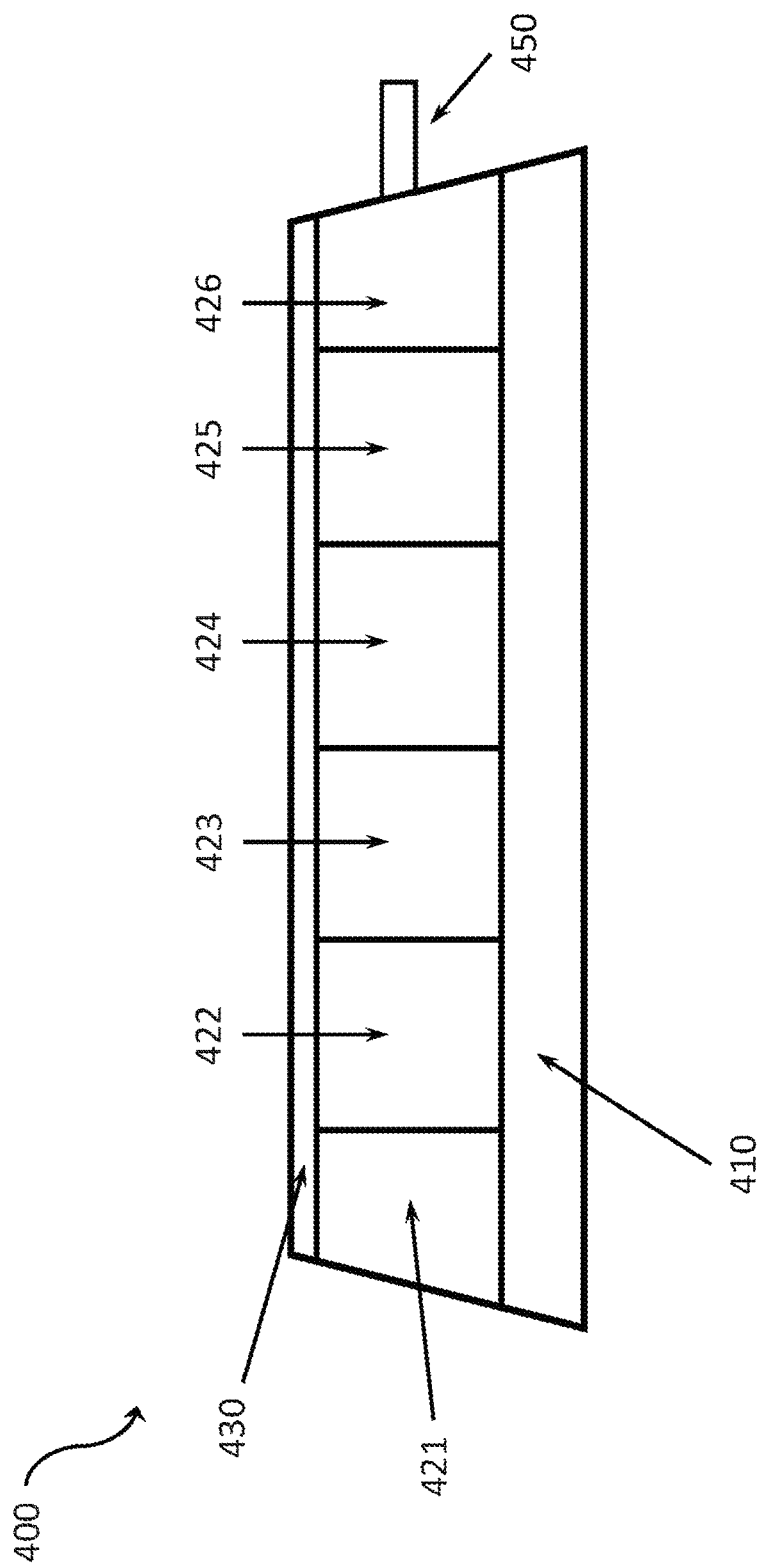
FIG. 7A shows a tracheostomy support system according to one embodiment.

FIG. 7A shows a view of an example embodiment of a tracheostomy support system in accordance with the technology described in the present application, labeled system 400. The system 400 comprises a multilayered pad configured to be disposed between a shield of a tracheostomy tube and a neck of a person, and includes:
- a first layer of material 410 configured to provide contact with the neck of a person;
- a second layer of material 430 configured to provide contact with the shield of a tracheostomy tube;
- an expandable compartment 421 disposed between the first layer of material 410 and the second layer of material 430; and
- at least another expandable compartment 422 disposed between the first layer of material 410 and the second layer of material 430.

FIG. 7A shows that the system 400 also includes expandable compartments 423-426 disposed between the first layer of material 410 and the second layer of material 430. A tracheostomy support system in accordance with the technology described in the present application can have any number of expandable compartments which can be larger or smaller than the number of compartments shown in FIG. 7A.

FIG. 7A also shows that, in some implementations, the system 400 is configured to have an interface 450 which can be used to inflate or deflate at least one of the expandable compartments. For example, in some implementations of the system 400, the interface 450 is configured for addition or removal of a gas to or from at least one of the expandable compartments. For example, in some implementations of the system 400, the interface 450 is configured for addition or removal of a liquid to or from at least one of the expandable compartments. For example, in some implementations of the system 400, the interface 450 is configured for addition or removal of a gas or a liquid (or both, separately or simultaneously) to or from at least one of the expandable compartments. In some implementations of the system 400, addition or removal of a gas (or a liquid, or both, separately or simultaneously) to or from at least one of the expandable compartments (e.g., compartment 421) is performed independently from addition or removal of a gas (or a liquid, or both, separately or simultaneously) to or from at least another expandable compartment (e.g., compartment 422).

Figure 7B:
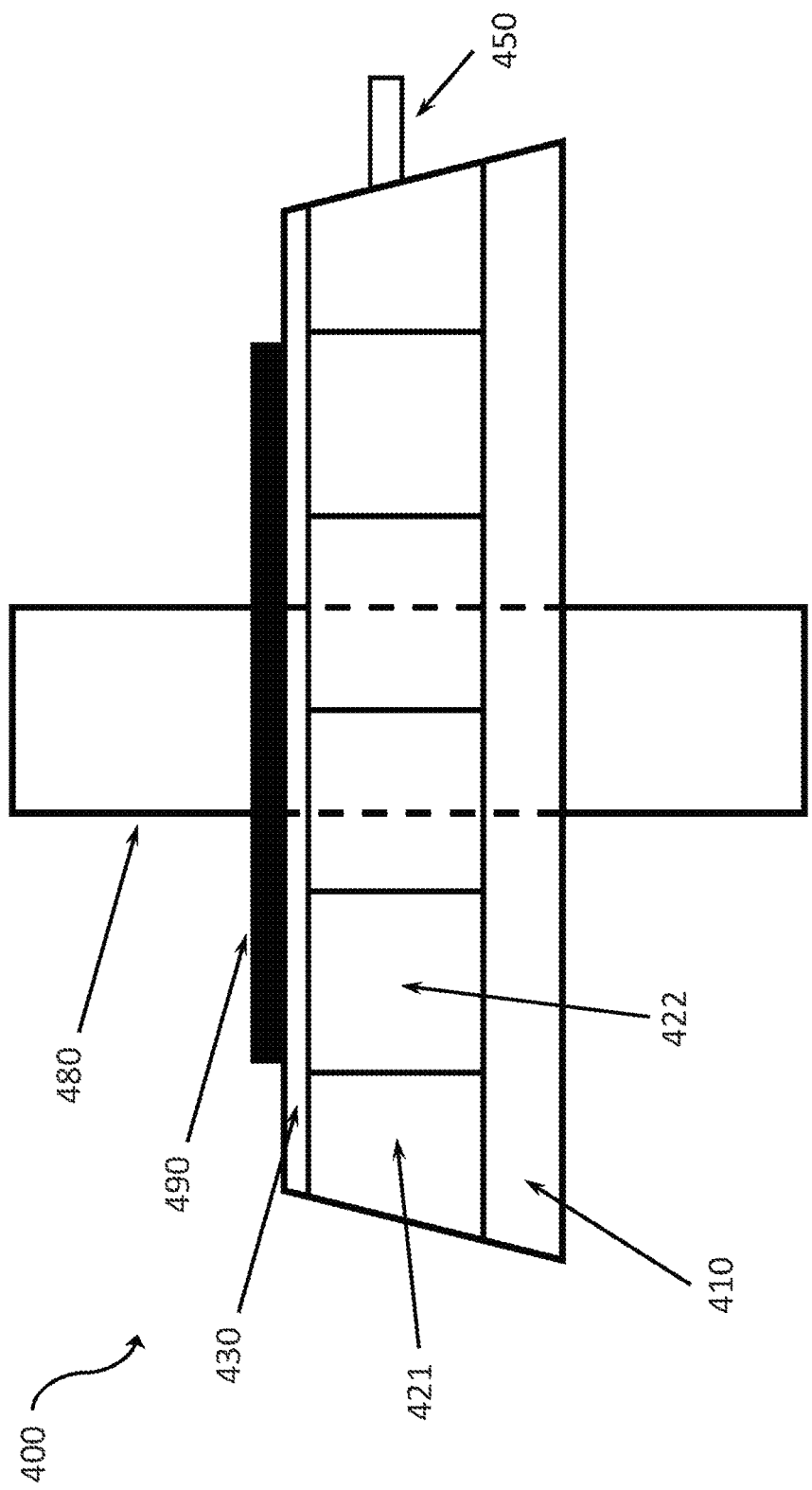
FIG. 7B shows the tracheostomy support system according to the embodiment shown in FIG. 7A interfaced with a tracheostomy tube.

FIG. 7B shows a view of the system 400 interfaced with a tracheostomy tube. FIG. 7B shows that the second layer of material 430 of the system 400 has a contact with the shield 490 of the tracheostomy tube 480.

Note that in some implementations, the system 400 has a single expandable compartment disposed between the first layer of material and the second layer of material.

Figure 8:
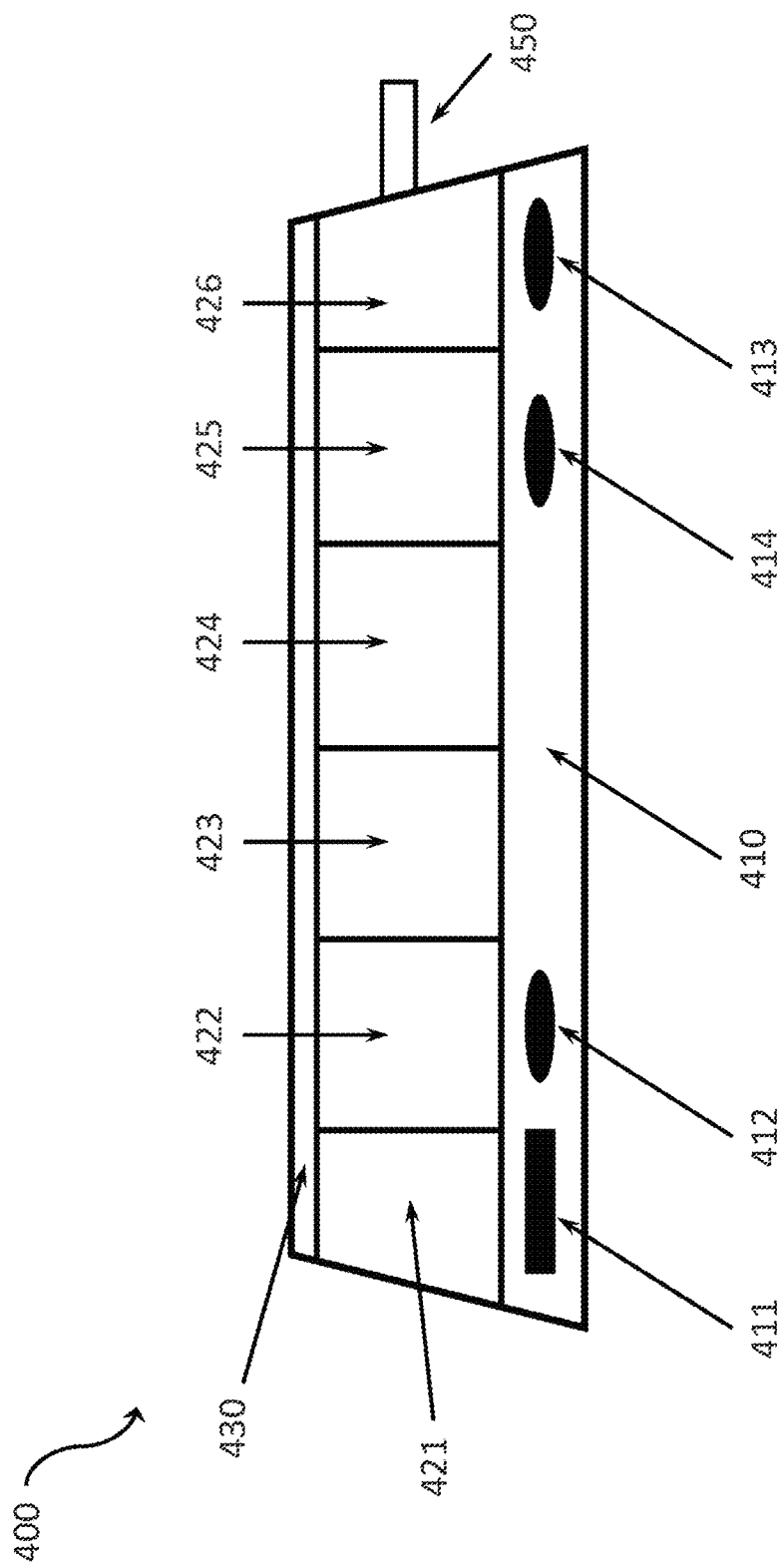
FIG. 8 shows a tracheostomy support system according to some embodiments.

FIG. 8 shows that, in some implementations, the system 400 includes at least one actuator 411 configured to produce vibrational movements.

FIG. 8 also shows that, in some implementations, the system 400 includes at least one chemical sensor 412 configured to sense at least one of:
- an ion concentration,
- a protein concentration,
- a creatine phosphokinase (CPK) concentration,
- a hypoxia-induced factor 1 alpha (HIF1-alpha) concentration,
- a matrix metalloproteinases (MMP) concentration,
- a zinc concentration, or
- a pH level.

FIG. 8 further shows that, in some implementations, the system 400 includes at least one sensor 413 configured to sense moisture.

FIG. 8 shows that, in some implementations, the system 400 includes at least one sensor 414 configured to sense pressure.

FIG. 8 illustrates that, in some implementations, the sensors of the system 400 are at least partially embedded into the first layer of material 410. In some implementations of the system 400, at least one of the sensors of the system 400 is configured for contact with the skin of the person who is using the tracheostomy support system 400.

In any of the embodiments and/or implementations of a tracheostomy support system in accordance with the technology disclosed in the present application, any of the sensors included in or embedded into the tracheostomy support system or otherwise interfaced with the tracheostomy support system can be included or embedded or otherwise interfaced with any of the layers, sections, or compartments of the tracheostomy support system or with any of
- a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube.

Figure 9A:
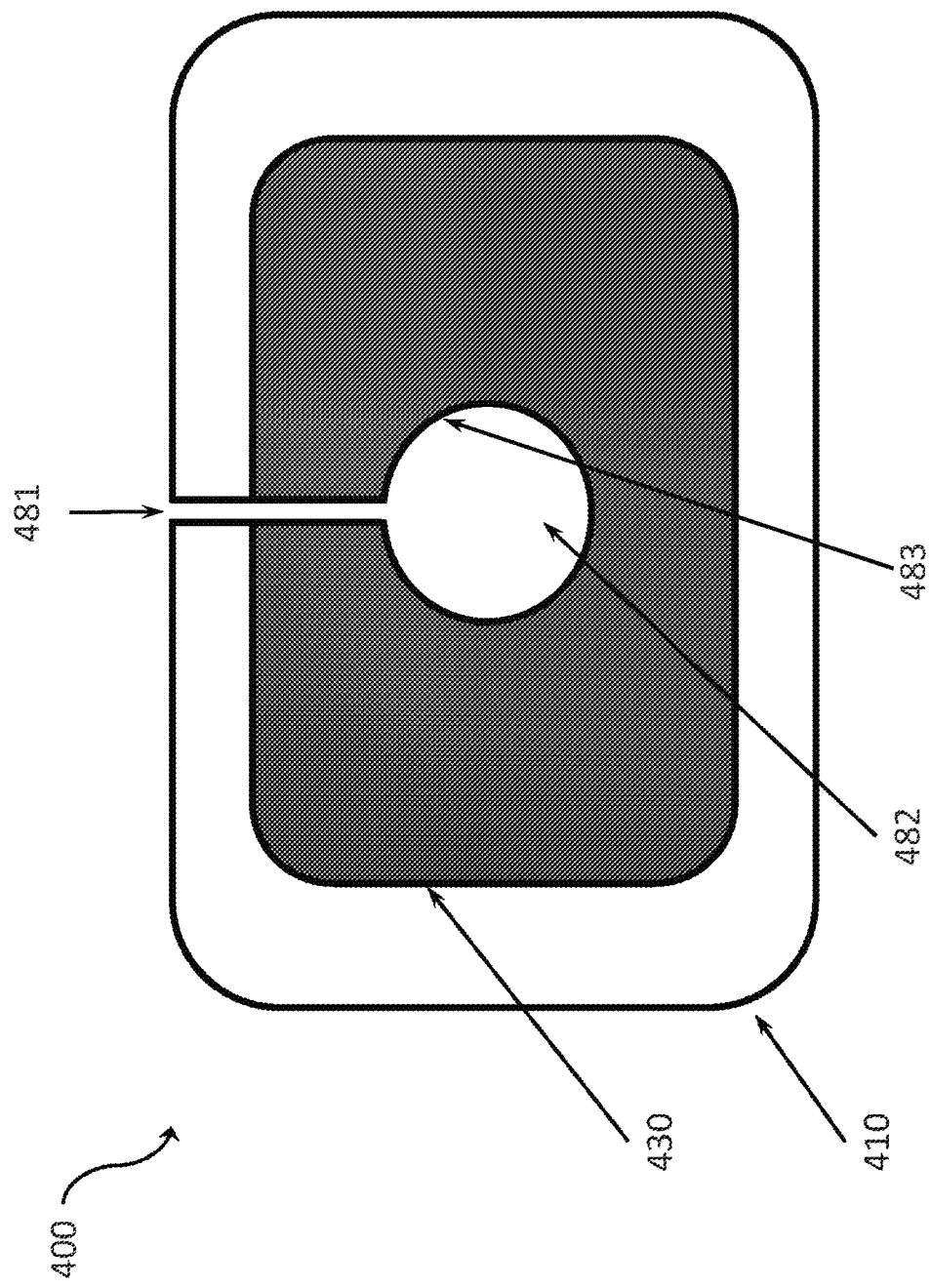
FIG. 9A shows another view of the tracheostomy support system according to the embodiment shown in FIG. 7A.

FIG. 9A shows a top view of the system 400 shown in FIG. 8A. FIG. 9A illustrates that the system 400 has a hollow channel 482 going through the system 400 and having inner surface 483 which is configured to interface with a tracheostomy tube inserted in the channel 482. FIG. 9A also shows that the system 400 has a discontinuity 481 in its structure coupled to the channel 482 and adapted to assist insertion of a tracheostomy tube into the channel 482. The elements 481 and 482, for example, of the system 400 as well as the materials used to manufacture the system 400 can be also adapted to allow the system 400 to use tracheostomy tubes of different sizes. Such materials can provide various elements of the system with a sufficiently high degree of stretchability and/or elasticity to facilitate use of tracheostomy tubes of different sizes.

Figure 9B:
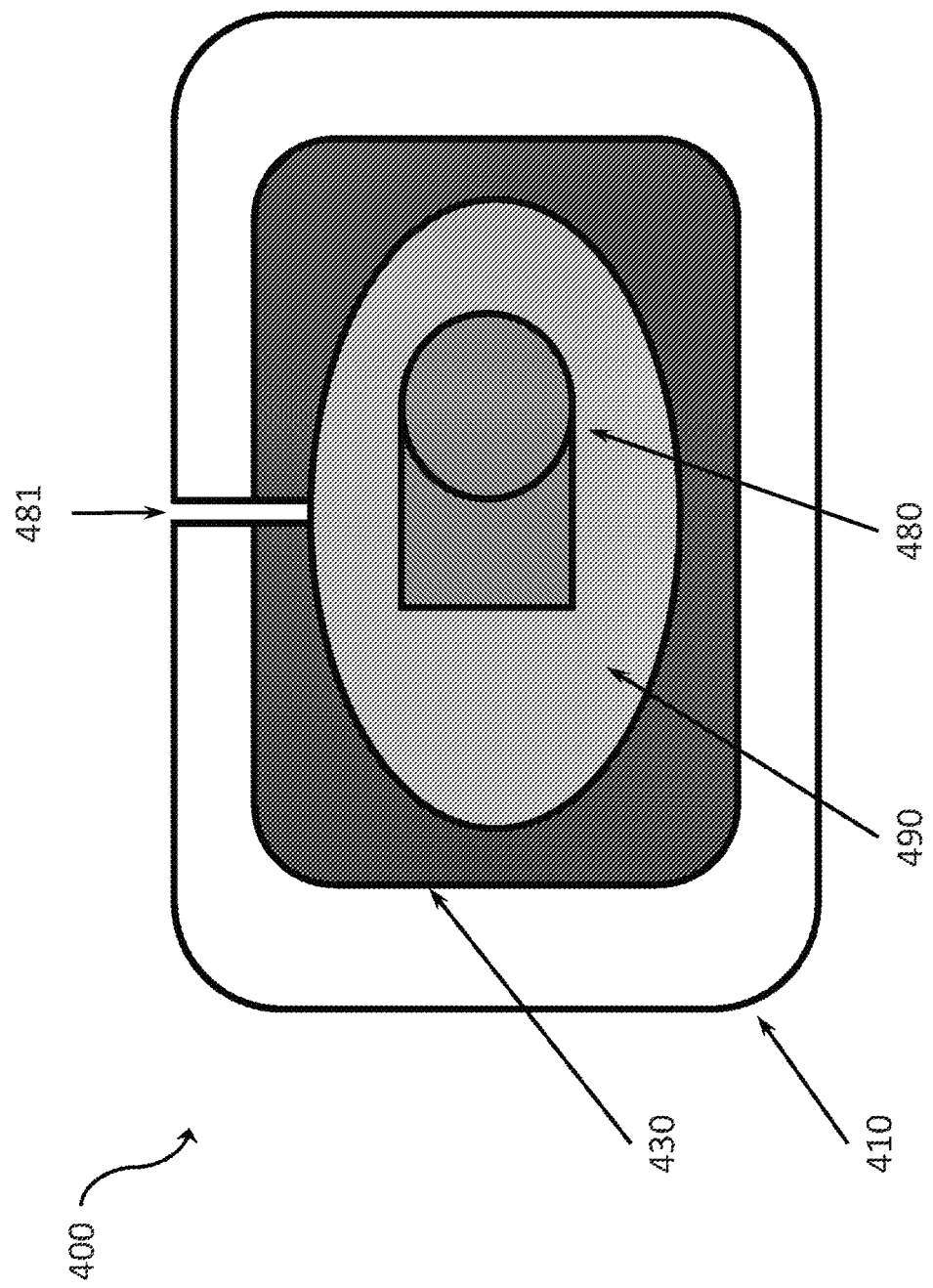
FIG. 9B shows a view of the tracheostomy support system according to the embodiment shown in FIG. 7A interfaced with a tracheostomy tube.

FIG. 9B shows a top view of the system 400 interfaced with a tracheostomy tube 480. FIG. 9B shows a shield 490 of the tracheostomy tube 480 disposed on the second layer of material 430 of the system 400.

FIGS. 7B and 9B show the tracheostomy support system according to some embodiments as it interfaces with a tracheostomy tube. The tracheostomy support system shown in FIGS. 7A, 7B, 8, 9A, and 9B is implemented as a multilayer pad including a first layer of material 410 configured to contact neck skin, a second layer of material 430 configured to provide contact with the shield of a tracheostomy tube, and an expandable compartment (e.g., 421) disposed between the first layer of material 410 and the second layer of material 430. FIG. 8 shows that some embodiments of the tracheostomy support system can include motorized actuators and/or biosensors or other sensors. For example, a tracheostomy support system can include at least one actuator configured to produce vibrational movements. For example, a tracheostomy support system can include at least one sensor configured to sense moisture. For example, a tracheostomy support system can include at least one sensor configured to sense pressure. These sensors and/or actuators can be embedded, for example in the first layer of material of the tracheostomy support system.

The tracheostomy support system can offload pressure caused by the tracheostomy tube on the neck skin of the patient. Additionally, the tracheostomy support system can indicate when pressure or moisture on the skin is at an unsafe level that may predispose the patient to neck skin ulceration, breakdown, or infection. The tracheostomy support system can be automatically adjusted through a closed-loop feedback system or manually adjusted.

The thickness of the multilayer pad may be adjusted by its expandable layer or its expandable compartments. The thickness may be automatically or manually adjusted within a defined range. Different thicknesses of pads may be used to best fit the posture and build of the patient. A piston, pump, turbine, knob, syringe, or the like may cause the contraction or expansion of the expandable layer by adding or removing a gas (e.g., air) or a liquid (e.g., water). The piston, pump, turbine, knob, syringe, aerosol, or the like may be driven by a motor for automatic adjustment to the thickness or height of the expandable layer.

The perimeter/shape of the multilayer pad can take many forms. The shape may be a square, rectangle, oval, circle, trapezoid, rhombus. The multilayer pad can have any other shape. The edges of the pad may be beveled or chamfered in a divergent fashion toward the neck skin, increasing the surface area of the side of the pad in direct contact with the patient's neck skin to further reduce pressure. This increase in the surface area of the multilayer pad against the neck skin dissipates pressure forces with greater efficiency.

The multilayer pad can be made, for example, of disposable materials such as the ones mentioned above. For instance, the multilayer pad can be made of disposable materials for single use on a single patient before being thrown away. For example, the multilayer pad can be made of durable and recyclable materials for reuse or more prolonged use. The multilayer pad can be latex-free, soft, and contain some grip to prevent movement against the neck skin of the patient.

The top layer can be made using a stiff but malleable material such as a plastic or silicone. The material allows pressure from the tracheostomy tube to be distributed evenly along the top layer of the pad (e.g., the second layer of material 430 in FIG. 7A) to its lower layers (e.g., the first layer of material 410 and the at least one expandable compartment 421 in FIG. 7A).

Lower layers of the pad can be preferably made of softer materials, especially those that come into contact with the neck skin. Lower layers dampen and redistribute the pressure against the multilayer pad. To this end, the lower layers of the multilayer pad may expand and contract to counteract the pressure from the tracheostomy tube.

The multilayer pad can include motorized actuators or haptic feedback-like devices, such as a vibration motor or actuator, including an eccentric rotating mass (ERM) actuator, that can provide macro, micro, or ultrasonic vibrations on the neck skin. This vibration or haptic feedback improves blood flow and stimulates neck skin tissues, ultimately preventing tissue necrosis, ulceration, and further breakdown. These actuators can be selectively activated by a feedback system or through user input. The actuators can be automatically activated by a sensor (e.g., a pressure sensor). The sensor can detect a region of neck skin that is vulnerable to injury or breakdown. The motorized actuators can be organized in various patterns (e.g., a grid pattern) for selectively targeting a region of the neck skin.

The multilayer pad may include a pressure sensor. The sensor may be placed, for example, between the multilayer pad and the patient, within the multilayer pad, or on the top material of the multilayer pad. The pressure sensor monitors pressure changes of the tracheostomy tube on the neck of the patient. In some embodiments, the pressure sensor will emit a signal if the amount of pressure exceeds a certain threshold. In some embodiments, the pressure sensor will emit a signal if the amount of pressure from the tracheostomy tube could develop a pressure wound or ulcer. An additional sensor may be used to emit a signal if a pressure wound or an ulcer is detected. Such sensor may detect changes in ion concentration, proteins, such as creatine phosphokinase (CPK), Hypoxia-induced factor 1 alpha (HIF1-alpha), matrix metalloproteinases (MMP), Zinc, pH using surface electrodes (e.g., flat ones), skin potential, skin conductance, skin resistance or impedance.

The pressure sensor can be communicatively coupled to the expandable layer of the multilayer pad. The pressure sensor can be communicatively coupled to a motor or a system which can add or remove a gas or a liquid (or both, simultaneously or independently) to or form the expandable layer. The pressure sensor can provide feedback for the expansion/contraction of the expandable layer in the multilayer pad. This feedback helps to counteract the torques and pressure forces that may be exerted by the tracheostomy tube on the neck skin of a person and thus helps to prevent damage to the neck skin of the patient, the soft tissues, the trachea, and the esophagus.

The pressure sensor may be communicatively coupled to the motorized actuators of the multilayer pad. The sensor can send a signal to the motorized actuators to stimulate an at-risk region of the neck skin. In some embodiments, a temperature sensor can send a signal for cooling or heating the multilayer pad to thus cool or heat the at-risk region of the neck skin.

The pressure sensor may be coupled to a memory. The memory stores data related to the signals generated by the sensor. The data stored in the memory can be retrievable. Certain data patterns can signal an alarm for examination and investigation by a clinician.

The pressure sensor can be communicatively coupled to a network containing a computer. The pressure sensor can send signals indicating the status of the patient to the computer through the network. The pressure sensor can include an indicator. The indicator can utilize a color, symbol, or alphanumeric output to convey information. The indicator can be externally displayed or emitted at the pressure sensor. In addition, information conveyed via the indicator can be communicated to the computer through the network. Information conveyed can include, for example, at least one of normal metric readings, abnormal metric readings, or pressure trends over time, among other types of information. In some embodiments, the indicator includes or is communicatively coupled to an alarm that can be audible, palpable, or visual. An alarm signal can be sent, for example, wirelessly to the computer, a patient's bed monitor, a nurses' station, or elsewhere through the network.

The pressure sensor or other sensors and/or actuators embedded into or otherwise interfaced with the multilayer pad can be communicatively coupled to the expandable layer. The pressure sensor or other sensors and/or actuators embedded into or otherwise interfaced with the multilayer pad can be communicatively coupled to a motor or a system which can add or remove a gas or a liquid (or both, independently or simultaneously) to or form the expandable layer. Such sensors and/or actuators can provide feedback for the expansion/contraction of the expandable layer in the multilayer pad.

In some embodiments, when the pressure sensor detects excessive pressure on the lower part of the patient's neck from the tracheostomy tube, a signal, in response to the sensor detection, is sent to the motor to raise the height or support of the expandable layer. This additional support relieves pressure on the patient from the tracheostomy tube. In some embodiments, when the sensor detects excessive pressure on the upper part of the patient's neck from the tracheostomy tube, a signal, in response to the sensor detection, is sent to the motor to lower the height or support of the expandable layer.

In some embodiments, when the pressure sensor detects excessive pressure on the lower part of the patient's neck from the tracheostomy tube, a signal, in response to the sensor detection, is sent to the motor to lower the height or support of the expandable layer. In some embodiments, when the sensor detects excessive pressure on the upper part of the patient's neck from the tracheostomy tube, a signal, in response to the sensor detection, is sent to the motor to raise the height or support of the expandable layer.

A computer may receive signals from the pressure sensor. The computer may respond differently to the sensor depending on a mode. For instance, a mode may sound an alarm if a signal or a set of signals is received by the computer. A particular mode may direct the expandable layer to respond according to the feedback provided by the sensor. The pressure sensor may be activated or deactivated.

Figure 10:
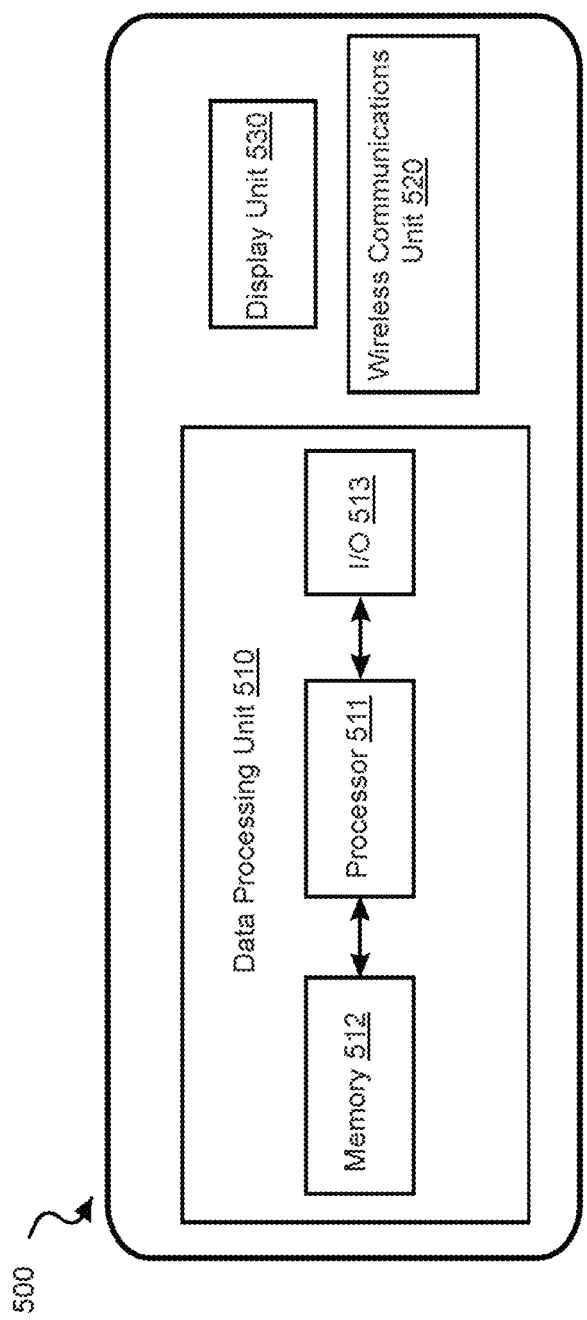
FIG. 10 shows a block diagram of an example embodiment of an electronic device that can interface with various elements of various embodiments of the tracheostomy support system for various implementations.

FIG. 10 shows a block diagram of an example embodiment of an electronic device 500 that can interface with various elements of various embodiments of the tracheostomy support system according to the technology disclosed in the present application.

For example, the electronic device 500 can be configured to be communicatively coupled to at least one pressure sensor and further configured to be communicatively coupled to a device (a "pump device") which controls the amount of a gas or a liquid in at least one expandable compartment of a tracheostomy support system according to the disclosed technology.

For example, the electronic device 500 can be configured to receive pressure data from the at least one pressure sensor in a form of digital or analog signals and further configured, based on the pressure data, cause the pump device to either remove or add the gas or the liquid into or from the at least one expandable compartment of the tracheostomy support system.

For example, the electronic device 500 can be configured to be communicatively couplet to at least one pressure sensor and further configured to be communicatively coupled to a device (a "pump device") which controls the amount of a gas or a liquid in at least one expandable layer of material of a tracheostomy support system according to the disclosed technology.

For example, the electronic device 500 can be configured to receive pressure data from the at least one pressure sensor in a form of digital or analog signals and further configured, based on the pressure data, cause the pump device to either remove or add the gas or the liquid into or from the at least one expandable layer of material of the tracheostomy support system.

For example, the electronic device 500 can be configured to control addition or removal of a gas or a liquid to or from at least one expandable compartment of a tracheostomy support system and control addition or removal of a gas or a liquid to or from at least another expandable compartment of the tracheostomy support system. For example, the electronic device 500 can be configured to control addition or removal of a gas or a liquid to or from at least one expandable compartment of a tracheostomy support system independently from addition or removal of a gas or a liquid to or from at least another expandable compartment of the tracheostomy support system.

In various implementations, the electronic device 500 is operable to store and execute software applications and algorithms and implement various controls of a tracheostomy support system according to the technology disclosed in the present application. In various implementations, the electronic device 500 can be implemented as a portable computing device, such as a mobile communications device, such as a smartphone, tablet or wearable device, like a smartwatch, glasses, etc.; and/or the electronic device 500 can be implemented as a stationary computing device, such as a desktop computer.

In some embodiments, the electronic device 500 includes a dongle that couples to at least one sensor or actuator of the tracheostomy support system to wirelessly connect to the computing components (e.g., a data processing unit) of the electronic device 500.

In some embodiments, the electronic device 500 uses its wireless communications unit 520 to connect to at least one sensor or actuator of the tracheostomy support system.

In some embodiments, the electronic device 500 uses its input/output unit (I/O) 513 to connect to at least one sensor or actuator of the tracheostomy support system.

In some embodiments, the electronic device 500 includes a data processing unit 510 which includes a processor 511 to process data, a memory 512 in communication with the processor 511 to store data, and an input/output unit (I/O) 513 to interface the processor 511 and/or the memory 512 to other modules, units or devices, including other external computing devices. For example, the processor 511 can include a central processing unit (CPU) or a microcontroller unit (MCU) or a graphics processing unit (GPU). For example, the memory 512 can include and store processor-executable code, which, when executed by the processor, configures the data processing unit 510 to perform various operations, e.g., such as receiving information, commands, and/or data, processing information, commands, and/or data, and transmitting or providing information, commands, and/or data to another device.

In some implementations, the electronic device 500 can transmit raw or processed data to a computer system or communication network accessible via the Internet (referred to as 'the cloud') that includes one or more remote computational processing devices (e.g., servers in the cloud).

To support various functions of the data processing unit 510, the memory 512 can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory 512.

In some embodiments, the data processing unit 510 includes a wireless communication unit 520, such as a wireless transmitter to transmit stored and/or processed data or a wireless transceiver (Tx/Rx) to transmit and receive data. The I/O 513 of the data processing unit 510 can interface the data processing unit 510 with the wireless communications unit 520 to utilize various types of wired or wireless interfaces compatible with typical data communication standards, for example, which can be used in communications of the data processing unit 510 with other devices, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE/5G cellular communication methods, NFC (Near Field Communication), and parallel interfaces.

In some embodiments, the data processing unit 510 includes a display unit 530, which can include a visual display such as a display screen, an audio display such as a speaker, or other type of display or combinations thereof.

The I/O 513 of the data processing unit 510 can also interface with other external interfaces, sources of data, data storage devices, and/or visual or audio display devices, etc. to retrieve and transfer data and information that can be processed by the processor 511, stored in the memory 512, or exhibited on an output unit (e.g., display unit 530) of the electronic device 500 or an external device. For example, the display unit 530 can be configured to be in data communication with the data processing unit 510, e.g., via the I/O 513, to provide a visual display, an audio display, and/or other sensory display that produces the user interface of the software application. In some examples, the display unit 530 can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

FIG. 11 shows an example embodiment of a tracheostomy support system in accordance with the technology described in the present application, labeled system 100. The system 100 is disposed on the chest 1 of a person 2 positioned on a support surface 3. The system 100 is interfaced with a tube 160 of a ventilator circuit of a lung ventilator. The tube 160 is connected to a tracheostomy tube T. FIG. 11 shows that a sensor S can be placed proximate to the tracheostomy tube T. For example, the sensor S can be one of a pressure sensor, a chemical sensor, or a moisture sensor. The sensor S can be a sensor of any other type. The sensor S can be communicatively coupled to the electronic device 500 described above and shown in FIG. 10.

As FIG. 11 illustrates, a pressure sensor can be positioned between the tracheostomy tube and the neck of the patient. The sensor monitors pressure changes of the tracheostomy tube on the neck of the patient. In some embodiments, the pressure sensor will emit a signal if the amount of pressure exceeds a certain threshold. In some embodiments, the pressure sensor will emit a signal if the amount of pressure from the tracheostomy tube could develop a pressure wound or ulcer. An additional sensor can be used to emit a signal if a pressure wound or an ulcer is detected. Such sensor can detect changes in ion concentration, proteins, such as creatine phosphokinase (CPK), Hypoxia-induced factor 1 alpha (HIF1-alpha), matrix metalloproteinases (MMP), Zinc, pH using surface electrodes (e.g., flat ones), skin potential, skin conductance, skin resistance or impedance.

In any of the embodiments, various sensors may be used including chemical sensors as detailed above, moisture, light and or temperature sensors. These sensors may monitor for chemical or temperature changes in the neck skin. They can have the same capabilities for interfacing with computers and networks as the pressure sensor.

The pressure sensor can be coupled to a memory. The memory stores data related to the signals generated by the sensor. The data stored in the memory can be retrievable. Certain data patterns can signal an alarm for examination and investigation by a clinician.

The pressure sensor can be communicatively coupled to a network containing a computer. The pressure sensor can send signals indicating the status of the patient to a computer through the network. The pressure sensor can include an indicator. The indicator can utilize a color, symbol, or alphanumeric output to convey information. The indicator can be externally displayed or emitted at the pressure sensor. In addition, information conveyed via the indicator may be communicated to the computer through the network. Information conveyed can include, for example, normal metric readings, abnormal metric readings, or pressure trends over time, among other types of information. In some embodiments, the indicator includes an alarm that can be audible, palpable, or visual. The alarm can be sent wirelessly to a computer, a patient's bed monitor, a nurses' station, or elsewhere through the network.

For example, the pressure sensor or other sensors and/or actuators embedded into or otherwise interfaced with a tracheostomy support system and/or a tube of a ventilator circuit of a lung ventilator, and/or a connection of a ventilator circuit of a lung ventilator, and/or an element of a ventilator circuit of a lung ventilator, and/or an element of a lung ventilator, and/or a tracheostomy tube, and/or a connection of a tracheostomy tube, and/or an element of a tracheostomy tube and/or a skin of a person can be communicatively coupled to a motor or a system which can add or remove a gas to or form the expandable layer or at least one expandable compartment of the tracheostomy support system, and can provide feedback for the expansion/contraction of the expandable layer or at least one expandable compartment of the tracheostomy support system.

In some embodiments, a pressure sensor detects excessive pressure on the lower part of the patient's neck from the tracheostomy tube. A signal, in response to the sensor detection, is sent to the motor to raise the height or support of the expandable layer. This additional support relieves pressure on the patient from the tracheostomy tube. In some embodiments, the pressure sensor detects excessive pressure on the upper part of the patient's neck from the tracheostomy tube. A signal, in response to the sensor detection, is sent to the motor to lower the height or support of the expandable layer. This decreased support relieves pressure on the patient from the tracheostomy tube.

A computer may receive the signals of the pressure sensor. The computer may respond differently to a sensor depending on a mode. For instance, a mode may sound an alarm if a signal or a set of signals is received by the computer from the sensor. A particular mode may direct the motor or the system which can add or remove a gas to or form the expandable layer or at least one expandable compartment of the tracheostomy support system to respond according to the feedback provided by the sensor.

The expandable layer or at least one expandable compartment of the tracheostomy support system can be operable independent of the signals from the pressure sensor. The pressure sensor may be activated or deactivated. The pressure sensor may be temporarily silenced or deactivated by a manual override.

Various embodiments of the tracheostomy support system can incorporate a vibration mechanism, such as, for example, a vibration motor or actuator, including an eccentric rotating mass (ERM) actuator. The vibration mechanism provides intermittent vibrations to stimulate circulation and avoid excess static pressure. These can be arranged, for example, in a grid-like pattern proximate to the base of the tracheostomy tube. A gyroscope may also be incorporated to prevent the system from shifting. This and an accelerometer may be used to calibrate the ideal position of the tracheostomy tube from which deviations will signal a notification or alarm. A fastener may be attached to the system (e.g., to one of its layers of material, or one of its sections, or one of its compartments) that may clip or fasten to the patient's garment or blanket to reduce movement.

EXAMPLES

The following examples may be preferable features of some implementations.

In some embodiments in accordance with the disclosed technology (Example E1), a tracheostomy support system (TSS or TS system below) comprises a multilayered pad configured to be disposed between a shield of a tracheostomy tube and a neck of a person. The multilayered pad includes:
  a first layer of material configured to provide contact with the neck of a person,
  a second layer of material configured to provide contact with the shield of a tracheostomy tube, and
  at least one expandable compartment disposed between the first layer of material and the second layer of material.

In some embodiments in accordance with the disclosed technology (Example E2), a TS system comprises a multilayered pad configured to be disposed between a shield of a tracheostomy tube and a neck of a person, wherein the multilayered pad includes:
  a first layer of material configured to provide contact with the neck of a person,
  a second layer of material configured to provide contact with the shield of a tracheostomy tube, and
  an expandable layer of material disposed between the first layer of material and the second layer of material.

In some embodiments in accordance with the disclosed technology (Example E3), a TS system comprises a multilayered pad configured to be disposed between a shield of a tracheostomy tube and a neck of a person. The multilayered pad includes:
  a layer of material configured to provide contact with the neck of a person, and
  at least one expandable compartment disposed on the layer of material and configured to provide contact with the shield of a tracheostomy tube.

In some embodiments in accordance with the disclosed technology (Example E4), a TS system comprises a multilayered pad configured to be disposed between a shield of a tracheostomy tube and a neck of a person. The multilayered pad includes:
  a layer of material configured to provide contact with the neck of a person, and
  an expandable layer of material disposed on the layer of material and configured to provide contact with the shield of a tracheostomy tube.

In some embodiments in accordance with the disclosed technology (Example E5), a tracheostomy support system includes:
  a base section;
  a top section; and
  at least one expandable compartment disposed between the base section and the top section.

In some embodiments in accordance with the disclosed technology (Example E6), a tracheostomy support system includes:
  a base section;
  a top section; and
  an expandable layer of material disposed between the base section and the top section.

In some embodiments in accordance with the disclosed technology (Example E7), a tracheostomy support system includes:
  a base section; and
  at least one expandable compartment disposed on the base section.

In some embodiments in accordance with the disclosed technology (Example E8), a tracheostomy support system includes:
  a base section;
  an expandable layer of material disposed on the base section.

Example E9 includes the tracheostomy support system as in any of examples E5-E8, wherein the base section is configured to be disposed on one of:
  a chest of a person, a table, or an articulated stand.

In the examples below, the term "the contact elements" can and should be replaced by:
  "a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube".

Example E10 includes the tracheostomy support system as in example E5 or example E6, wherein the top section is configured for contact with at least one of the contact elements.

Example E11 includes the tracheostomy support system as in example E7, wherein the at least one expandable compartment is configured for contact with at least one of the contact elements.

Example E12 includes the tracheostomy support system as in example E8, wherein the expandable layer of material is configured for contact with at least one of the contact elements.

Example E13 includes the tracheostomy support system as in example E5 or example E6, wherein the top section is configured to have a trough adapted for contact with at least one of the contact elements.

Example E14 includes the tracheostomy support system as in example E5 or example E6, wherein the top section is configured to have a hollow channel inside the top section, wherein the hollow channel is adapted for contact with at least one of the contact elements.

Example E15 includes the tracheostomy support system as in example E7, wherein the at least one expandable compartment is configured to have a trough adapted for contact with at least one of the contact elements.

Example E16 includes the tracheostomy support system as in example E7, wherein the at least one expandable compartment has a hollow channel inside the at least one expandable compartment, wherein the hollow channel is adapted for contact with at least one of the contact elements.

Example E17 includes the tracheostomy support system as in example E8, wherein the expandable layer of material is configured to have a trough adapted for contact with at least one of the contact elements.

Example E18 includes the tracheostomy support system as in example E8, wherein the expandable layer of material has a hollow channel inside the expandable layer of material, wherein the hollow channel is adapted for contact with at least one of the contact elements.

Example E19 includes the tracheostomy support system as in any of examples E1, E3, E5, E7, E11, E15, E16, or E20, wherein the at least one expandable compartment is configured to expand when a gas or a liquid is added to the at least one expandable compartment.

Example E20 includes the tracheostomy support system as in any of examples E1, E3, E5, E7, E11, E15, E16, or E19, wherein the at least one expandable compartment is configured to contract when a gas or a liquid is removed from the at least one expandable compartment.

Example E21 includes the tracheostomy support system as in any of examples E2, E4, E6, E8, E12, E17, E18, or E22, wherein the expandable layer of material is configured to expand when a gas or a liquid is added to the expandable layer.

Example E22 includes the tracheostomy support system as in any of examples E2, E4, E6, E8, E12, E17, E18, or E21, wherein the expandable layer of material is configured to contract when a gas or a liquid is removed from the expandable layer.

Example E23 includes the tracheostomy support system as in any of examples E1, E3, E5, E7, E11, E15, E16, E19, or E20, wherein the at least one expandable compartment of the system has a hollow interior.

Example E24 includes the tracheostomy support system as in any of examples E1, E3, E5, E7, E11, E15, E16, E19, E20, or E23, wherein the at least one expandable compartment of the system has an interior volume at least partially filled with a material.

Example E25 includes the tracheostomy support system as in any of examples E1, E3, E5, E7, E11, E15, E16, E19, E20, E23, E24, E26, or E27 wherein the system has an interface configured for addition or removal of a gas to or from the at least one expandable compartment.

Example E26 includes the tracheostomy support system as in any of examples E1, E3, E5, E7, E11, E15, E16, E19, E20, E23, E24, E25, or E27, wherein the system has an interface configured for addition or removal of a liquid to or from the at least one expandable compartment.

Example E27 includes the tracheostomy support system as in any of examples E1, E3, E5, E7, E11, E15, E16, E19, E20, E23, E24, E25, or E26, wherein the system has an interface configured for addition or removal of a gas or a liquid to or from the at least one expandable compartment.

Example E28 includes the tracheostomy support system as in any of examples E2, E4, E6, E8, E12, E17, E18, E21, or E22, wherein the expandable layer of the system has a hollow interior.

Example E29 includes the tracheostomy support system as in any of examples E2, E4, E6, E8, E12, E17, E18, E21, E22, or E28, wherein the expandable layer of the system has an interior volume at least partially filled with a material.

Example E30 includes the tracheostomy support system as in any of examples E2, E4, E6, E8, E12, E17, E18, E21, E22, or E28, wherein the expandable layer of the system is made of a porous material.

Example E31 includes the tracheostomy support system as in any of examples E2, E4, E6, E8, E12, E17, E18, E21, E22, E28, E29, E30, E32, or E33, wherein the system has an interface configured for addition or removal of a gas to or from the expandable layer.

Example E32 includes the tracheostomy support system as in any of examples E2, E4, E6, E8, E12, E17, E18, E21, E22, E28, E29, E30, E31, or E33, wherein the system has an interface configured for addition or removal of a liquid to or from the expandable layer.

Example E33 includes the tracheostomy support system as in any of examples E2, E4, E6, E8, E12, E17, E18, E21, E22, E28, E29, E30, E31, or E32, wherein the system has an interface configured for addition or removal of a gas or a liquid to or from the expandable layer.

Example E34 includes the tracheostomy support system as in any of examples E1, E3, E5, E7, E11, E15, E16, E19, E20, E23, E24, E25, E26, or E27, wherein the system includes at least one pressure sensor configured to be communicatively coupled to a device (a "pump device") which controls the amount of a gas or a liquid in the at least one expandable compartment of the tracheostomy support system.

Example E35 includes the tracheostomy support system as in any of examples E1, E3, E5, E7, E11, E15, E16, E19, E20, E23, E24, E25, E26, or E27, wherein the system includes at least one pressure sensor configured to be communicatively coupled to a control unit which is configured to be communicatively coupled to a device (a "pump device") which controls the amount of a gas or a liquid in the at least one expandable compartment of the tracheostomy support system.

Example E36 includes the tracheostomy support system as in example E34 or example E35, wherein at least one of the control unit or the pump device is configured to receive pressure data from the at least one pressure sensor in a form of digital or analog signals and is further configured, based on the pressure data, cause the pump device to remove or add the gas or the liquid into or from the at least one expandable compartment of the tracheostomy support system.

Example E37 includes the tracheostomy support system as in any of examples E2, E4, E6, E8, E12, E17, E18, E21, E22, E28, E29, E30, E31, E32, or E33, wherein the system includes at least one pressure sensor configured to be communicatively coupled to a device (a "pump device") which controls the amount of a gas or a liquid in the expandable layer of material of the tracheostomy support system.

Example E38 includes the tracheostomy support system as in any of examples E2, E4, E6, E8, E12, E17, E18, E21, E22, E28, E29, E30, E31, E32, or E33, wherein the system includes at least one pressure sensor configured to be communicatively coupled to a control unit which is configured to be communicatively coupled to a device (a "pump device") which controls the amount of a gas or a liquid in the expandable layer of material of the TS system.

Example E39 includes the tracheostomy support system as in example E37 or example E38, wherein at least one of the control unit or the pump device is configured to receive pressure data from the at least one pressure sensor in a form of digital or analog signals and is further configured, based on the pressure data, cause the pump device to remove or add the gas or the liquid to or from the expandable layer of material of the TS system.

Example E40 includes the tracheostomy support system as in any of examples E1, E3, E5, E7, E11, E15, E16, E19, E20, E23, E24, E25, E26, E27, E34, E35, or E36, wherein the tracheostomy support system includes at least another expandable compartment.

Example E41 includes the tracheostomy support system as in any of examples E40 or E42, wherein the at least another expandable compartment is configured to expand independently from the at least one compartment of the system.

Example E42 includes the tracheostomy support system as in any of examples E40 or E41, wherein the at least another expandable compartment is configured to contract independently from the at least one compartment of the system.

Example E43 includes the tracheostomy support system as in any of examples E40, E41, or E42, wherein the system has an interface configured for addition or removal of a gas to or from the at least one expandable compartment and for addition or removal of a gas to or from the at least another expandable compartment.

Example E44 includes the tracheostomy support system as in example E43, wherein the interface is configured to perform addition or removal of a gas to or from the at least one expandable compartment independently from the addition or removal of a gas to or from the at least another expandable compartment.

Example E45 includes the tracheostomy support system as in any of examples E40, E41, or E42, wherein the system has an interface configured for addition or removal of a liquid to or from the at least one expandable compartment and for addition or removal of a liquid to or from the at least another expandable compartment.

Example E46 includes the tracheostomy support system as in example E45, wherein the interface is configured to perform addition or removal of a liquid to or from the at least one expandable compartment independently from the addition or removal of a liquid to or from the at least another expandable compartment.

Example E47 includes the tracheostomy support system as in any of examples E40-E46, wherein the system includes at least one pressure sensor configured to be communicatively coupled to a device (a "pump device") which controls the amount of a gas or a liquid in the at least one expandable compartment and the at least another expandable compartment of the tracheostomy support system.

Example E48 includes the tracheostomy support system as in any of examples E40-E46, wherein the system includes at least one pressure sensor configured to be communicatively coupled to a control unit which is configured to be communicatively coupled to a device (a "pump device") which controls the amount of a gas or a liquid in the at least one expandable compartment and the at least another expandable compartment of the tracheostomy support system.

Example E49 includes the tracheostomy support system as in example E47 or example E48, wherein at least one of the control unit or the pump device is configured to receive pressure data from the at least one pressure sensor in a form of digital or analog signals and is further configured, based on the pressure data, cause the pump device to remove or add the gas or the liquid to or from the at least one expandable compartment and the at least another expandable compartment of the tracheostomy support system.

Example E50 includes the tracheostomy support system as in example E49, wherein at least one of the control unit or the pump device is configured to remove or add the gas or the liquid to or from the at least one expandable compartment independently from adding or removing the gas or the liquid to or from the at least another expandable compartment of the tracheostomy support system.

Example E51 includes the tracheostomy support system as in any of the preceding or the following examples, wherein the system includes at least one temperature sensor.

Example E52 includes the tracheostomy support system as in example E51, wherein the at least one temperature sensor is disposed in the first layer of material.

Example E53 includes the tracheostomy support system as in any of the preceding or the following examples, wherein the system includes at least one heating element.

Example E54 includes the tracheostomy support system as in example E51, wherein the system includes at least one heating element.

Example E55 includes the tracheostomy support system as in example E54, wherein the system includes a control unit communicatively coupled to the at least one heating element and the at least one temperature sensor and configured to control the at least one heating element using readings from the at least one temperature sensor.

Example E56 includes the tracheostomy support system as in any of the preceding or the following examples, wherein the system includes at least one chemical sensor configured to sense at least one of:
an ion concentration,
a protein concentration,
a creatine phosphokinase (CPK) concentration,
a hypoxia-induced factor 1 alpha (HIF1-alpha) concentration,
a matrix metalloproteinases (MMP) concentration,
a zinc concentration, or
a pH level.

Example E57 includes the tracheostomy support system as in any of the preceding or the following examples, wherein the system includes at least one sensor configured to sense moisture.

Example E58 includes the tracheostomy support system as in any of the preceding or the following examples, wherein the system includes a unit communicatively coupled to and configured to receive a reading in a form of a digital or analog signal from at least one of:
a pressure sensor,
a temperature sensor,
a chemical sensor,
a chemical sensor of example E56,
a sensor configured to sense moisture,
a sensor configured to sense skin potential,
a sensor configured to sense skin conductance,
a sensor configured to sense skin resistance, or
a sensor configured to sense skin impedance.

Example E59 includes the tracheostomy support system as in any of the preceding or the following examples, wherein the system includes an indicator element configured to emit at least one of:
an audible signal,
a palpable signal,
a visual signal,
an electric signal, or
an electromagnetic signal.

Example E60 includes the tracheostomy support system as in example 59, wherein the emission occurs when a reading from at least one of the sensors of Example 58 satisfies a condition.

Example E61 includes the tracheostomy support system as in any of the preceding or the following examples, wherein the at least one of:
the pressure sensor, the temperature sensor, the chemical sensor, or the moisture senor sensor
is disposed proximate to at least one of:
the base section, the at least one expandable compartment, the at least another expandable compartment, the expandable layer of material, the top section, the top layer, the first layer of material, the second layer of material, the tube of a ventilator circuit of a lung ventilator, the connection of a ventilator circuit of a lung ventilator, the element of a ventilator circuit of a lung ventilator, the element of a lung ventilator, the tracheostomy tube, the connection of a tracheostomy tube, or the element of a tracheostomy tube.

Example E62 includes the tracheostomy support system as in any of examples E34, E35, E36, E37, E38, E39, E47, E48, E49, or E50, wherein the at least one pressure sensor disposed proximate to a tracheostomy tube.

Example E63 includes the tracheostomy support system as in any of examples E34, E35, E36, E37, E38, E39, E47, E48, E49, E50, or E62, wherein the pressure sensor is configured to sense pressure.

Example E64 includes the tracheostomy support system as in any of examples E34, E35, E36, E37, E38, E39, E47, E48, E49, E50, or E62, wherein the pressure sensor is configured to sense pressure exerted on a neck skin of a person.

Example E65 includes the tracheostomy support system as in any of the preceding or the following examples, wherein the interface of the tracheostomy support system is disposed on at least one of:
the base section, the at least one expandable compartment, the at least another expandable compartment, the expandable layer of material, the top section, the top layer, the first layer of material, or the second layer of material.

Example E66 includes the tracheostomy support system as in any of the preceding or the following examples, wherein the system includes at least one actuator configured to produce vibrational movements.

Example E67 includes the tracheostomy support system as in any of the preceding or the following examples, wherein the system includes at least one gyroscope.

Example E68 includes the tracheostomy support system as in example 63, wherein the gyroscope is configured to provide motion stabilization for the tracheostomy support system.

Example E69 includes the tracheostomy support system as in example E58, wherein the unit is further communicatively coupled to and configured to receive a reading in a form of a digital or analog signal from at least one of:
a heating element,
an actuator configured to produce vibrational movements, or
a gyroscope.

Example E70 includes the tracheostomy support system as in example 59, wherein the emission occurs when a reading from at least one of:
a heating element,
an actuator configured to produce vibrational movements, or
a gyroscope
satisfies a condition.

(Example E71) A method of compensating a torque or a pressure exerted on a neck skin of a person which includes providing a tracheostomy support system as in any of the preceding examples.

(Example E72) A method of compensating a torque or a pressure exerted on a neck skin of a person including a tracheostomy support system as in any of the preceding examples.

(Example E73) A method of compensating a torque or a pressure exerted on a neck skin of a person including a tracheostomy support system as described in this patent document.

(Example E74) A material, article, device or method of manufacture thereof including a tracheostomy support system as described in this patent document.

(Example E75) A device, comprising:
a base;
an expandable layer formed over the base, the expandable layer capable of expanding by insertion of air or liquid; and
a top layer formed over the expandable layer, the top layer being configured to support a tube.

(Example E76) The device of any of the preceding or subsequent examples, wherein the expandable layer includes a composite material.

(Example E77) The device of any of the preceding or subsequent examples, wherein the expandable layer includes a compartment for receiving air or liquid.

(Example E78) The device of any of the preceding or subsequent examples, wherein the expandable layer includes one of a motor, pump, piston, or turbine for inserting air or liquid.

(Example E79) The device of any of the preceding or subsequent examples, wherein the expandable layer is communicatively coupled to a pressure sensor, the pressure sensor capable of sending a signal to expand the expandable layer.

(Example E80) The device of any of the preceding or subsequent examples, wherein the expandable layer includes an outflow valve, the outflow valve removing air or liquid from the expandable layer.

(Example E81) The device of any of the preceding or subsequent examples, wherein the broad base plate includes a vibration mechanism.

(Example E82) A device, comprising:
a multilayer pad;
an expandable layer within the multilayer pad, the expandable layer capable of expanding by insertion of air or liquid; and
a top layer within the multiplayer pad, the top layer being configured to support a tube.

(Example E82) The device of any of the preceding or subsequent examples, wherein the top layer is composed of a stiff but malleable material.

(Example E83) The device of any of the preceding or subsequent examples, further comprising:
a motorized actuator located in the multilayer pad, the motorized actuator capable of producing a vibration.

The term "target" in the text below can refer to at least one of:
a neck of a person,
a chest of a person,
an articulating stand,
a support arm,
a support table, or
a support surface.

It would be appreciated by one of skill in the art that various system configurations, apparatuses, devices, and methods that use these systems, devices, and apparatuses for tracheostomy support are described in this patent document.

Section headings are used in the present document only for ease of understanding and do not limit the scope of the embodiments to the section in which they are described. Subject matter described under one section heading may be combined with subject matter from other section headings.

The above description and drawings are illustrative and are not to be construed as limiting. Numerous specific details are described to provide a thorough understanding of the disclosure. However, in some instances, well-known details are not described in order to avoid obscuring the description. Further, various modifications may be made without deviating from the scope of the embodiments. Accordingly, the embodiments are not limited except as by the appended claims.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

The terms used in this specification generally have their ordinary meanings in the art, within the context of the disclosure, and in the specific context where each term is used. Terms that are used to describe the disclosure are discussed below, or elsewhere in the specification, to provide additional guidance to the practitioner regarding the description of the disclosure. For convenience, some terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. One will recognize that "memory" is one form of a "storage" and that the terms may on occasion be used interchangeably.

Consequently, alternative language and synonyms may be used for any one or more of the terms discussed herein, nor is any special significance to be placed upon whether or not a term is elaborated or discussed herein. Synonyms for some terms are provided. A recital of one or more synonyms does not exclude the use of other synonyms. The use of examples anywhere in this specification including examples of any term discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

While this patent document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

What is claimed are techniques and structures as described and shown, including:

1. A system, comprising:
    a base section;
    at least one expandable compartment disposed on the base section, wherein the at least one expandable compartment is configured to expand when a gas or a liquid is added to the at least one expandable compartment and the at least one expandable compartment is configured to contract when the gas or the liquid is removed from the at least one expandable compartment, and wherein the at least one expandable compartment is further configured to have a trough adapted for contact with at least one of:
    a tube of a ventilator circuit of a lung ventilator, a connection of a ventilator circuit of a lung ventilator, an element of a ventilator circuit of a lung ventilator, an element of a lung ventilator, a tracheostomy tube, a connection of a tracheostomy tube, or an element of a tracheostomy tube;
    an interface configured for addition or removal of at least one of:
        the gas,
        the liquid, or
        the gas and the liquid
    to or from the at least one expandable compartment; and
    at least one pressure sensor configured to be communicatively coupled to a device configured to control an amount of the gas or the liquid in the at least one expandable compartment.

2. The system of claim 1, further comprising at least another expandable compartment.

3. The system of claim 2, wherein the at least another expandable compartment is configured to expand and/or contract independently from the at least one compartment.

4. The system of claim 3, wherein the interface is further configured for addition or removal of the gas or the liquid to or from the at least another expandable compartment.

5. The system of claim 3, wherein the interface is further configured for addition or removal of the gas or the liquid to or from the at least one expandable compartment independently from the addition or removal of the gas or the liquid to or from the at least another expandable compartment.

6. The system of claim 1, further comprising at least one temperature sensor.

7. The system of claim 1, further comprising at least one heating element.

8. The system of claim 1, further comprising at least one chemical sensor configured to sense at least one of:
   an ion concentration,
   a protein concentration,
   a creatine phosphokinase (CPK) concentration,
   a hypoxia-induced factor 1 alpha (HIF1-alpha) concentration,
   a matrix metalloproteinases (MMP) concentration,
   a zinc concentration, or
   a pH level.

9. The system of claim 1, further comprising at least one sensor configured to sense moisture.

10. The system of claim 1, further comprising a unit communicatively coupled to and configured to receive a reading in a form of a digital or analog signal from at least one of:
   a pressure sensor,
   a temperature sensor,
   a chemical sensor,
   a sensor configured to sense moisture,
   a sensor configured to sense skin potential,
   a sensor configured to sense skin conductance,
   a sensor configured to sense skin resistance, or
   a sensor configured to sense skin impedance.

11. The system of claim 1, further comprising an indicator element configured to emit at least one of:
   an audible signal,
   a palpable signal,
   a visual signal,
   an electric signal, or
   an electromagnetic signal.

12. The system of claim 11, wherein the indicator element is configured to emit when a reading from at least one of:
   a pressure sensor,
   a temperature sensor,
   a chemical sensor,
   a sensor configured to sense moisture,
   a sensor configured to sense skin potential,
   a sensor configured to sense skin conductance,
   a sensor configured to sense skin resistance, or
   a sensor configured to sense skin impedance
satisfies a condition.

13. The system of claim 1, further comprising at least one actuator configured to produce vibrational movements.

14. The system of claim 1, further comprising at least one gyroscope.

15. The system of claim 14, wherein the gyroscope is configured to provide motion stabilization for the system.

16. The system of claim 10, wherein the unit is further communicatively coupled to and configured to receive a reading in a form of a digital or analog signal from at least one of:
   a heating element,
   an actuator configured to produce vibrational movements, or
   a gyroscope.

17. The system of claim 11, wherein the indicator element is configured to emit when a reading from at least one of:
   a heating element,
   an actuator configured to produce vibrational movements, or
   a gyroscope
satisfies a condition.

18. The system of claim 1, wherein the at least one pressure sensor is disposed proximate to a tracheostomy tube.

19. The system of claim 18, wherein the pressure sensor is configured to sense pressure exerted on a target.

* * * * *